(12) United States Patent
Chye et al.

(10) Patent No.: US 7,880,053 B2
(45) Date of Patent: Feb. 1, 2011

(54) METHODS OF USING TRANSFORMED PLANTS EXPRESSING PLANT-DERIVED ACYL-COENZYME-A-BINDING PROTEINS IN PHYTOREMEDIATION

(75) Inventors: Mee Len Chye, Hong Kong (CN); Shi Xiao, Hong Kong (CN); Wei Gao, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 301 days.

(21) Appl. No.: 12/062,077

(22) Filed: Apr. 3, 2008

(65) Prior Publication Data

US 2008/0289252 A1 Nov. 27, 2008

Related U.S. Application Data

(60) Provisional application No. 60/922,847, filed on Apr. 11, 2007.

(51) Int. Cl.
*C12N 15/29* (2006.01)
*C12N 15/82* (2006.01)
*A01H 5/00* (2006.01)
*A01H 5/10* (2006.01)

(52) U.S. Cl. .................. 800/278; 800/298; 800/295; 800/306; 435/419; 435/468; 435/252.33

(58) Field of Classification Search ................ None
See application file for complete search history.

(56) References Cited

U.S. PATENT DOCUMENTS

| 2002/0068825 A1 | 6/2002 | Au-Young et al. |
| 2005/0049201 A1 | 3/2005 | Lowe et al. |
| 2009/0291479 A1 | 11/2009 | Hong et al. |

OTHER PUBLICATIONS

Salt et al. Biotechnology, vol. 13, pp. 468-474, 1995.*
Guerinot et al. Plant Physiology (2001), vol. 125, pp. 164-167.*
Altschul et al. 1990. Basic local alignment search tool. J. Mol. Biol. 215: 403-410.
Benfey et al. 1989. The CaMV 35S enhancer contains at least two domains which can confer different developmental and tissue-specific expression patterns. EMBO J. 8(8):2195-2202.
Bradford, Marion M. 1976. A Rapid and Sensitive Method for the Quantitation of Microgram Quantities of Protein Utilizing the Principle of Protein-Dye Binding. Anal. Biochem. 72: 248-254.
Chiang et al. 1993. Mutagenic Oligonucleotide-directed PCR Amplification (Mod-PCR): An Efficient Method for Generating Random Base Substitution Mutations in a DNA Sequence Element. PCR Methods Appl. 2: 210-217.
Chye et al. 1998. Arabidopsis cDNA encoding a membrane-associated protein with an acyl-CoA-binding domain. Plant Mol. Biol. 38: 827-838.
Chye et al. 1999. Isolation of a gene encoding Arabidopsis membrane-associated acyl-CoA-binding protein and immunolocalization of its gene product. Plant J. 18(2): 205-214.

Chye et al. 2000. Single amino acid substitutions at the acyl-CoA-binding domain interrupt $^{14}$[C]palmitoyl-CoA binding of ACBP2, an Arabidopsis acyl-CoA-binding protein with ankyrin repeats. Plant Mol. Biol. 44: 711-721.
Clough, Steven J. and Bent, Andrew F. 1998. Floral dip: a simplified method for Agrobacterium-mediated transformation of *Arabidopsis thaliana*. Plant J. 16(6): 735-743.
Cobbett, C. et al. 2002. Phytochelatins and metallothioneins: Roles in heavy metal detoxification and homeostasis. Annu. Rev. Plant Biol. 53:159-182.
Coruzzi et al. 1984. Tissue-specific and light-regulated expression of a pea nuclear gene encoding the small subunit of ribylose-1,5-bisphosphate carboxylase. EMBO J. 3(8):1671-1679.
Dhankher et al. 2002. Engineering tolerance and hyperaccumulation of arsenic in plants by combining arsenate reductase and gamma-glutamylcysteine synthetase expression. Nature Biotech. 20: 1140-1146.
Dykema et al. 1999. A new class of proteins capable of binding transition metals. Plant Mol. Biol. 41: 139-150.
Engeseth et al. 1996. Characterization of an acyl-CoA-binding protein from *Arabidopsis thaliana*. Arch. Biochem. Biophys. 331:55-62.
Faergeman, Nils Joakim and Knudsen, Jens. 1997. Role of long-chain fatty acyl-CoA esters in the regulation of metabolism and in cell signalling. Biochem. J. 323: 1-12.
Funaba, Masayuki and Mathews, Lawrence S. 2000. Identification and characterization of constitutively active Smad2 mutants: evaluation of formation of Smad complex and subcellular distribution. Mol. Endocrinol. 14(10): 1583-1591.
Greener et al. 1995. An Efficient Random Mutagenesis Technique Using an *E. coli* Mutator Strain. Methods in Molecular Biology, 57:375-385. (First page only).
Horsch et al. 1985. A Simple and General-Method for Transferring Genes into Plants. Science 227: 1229-1231.
Kim et al. 2006. AtATM3 is involved in heavy metal resistance in Arabidopsis. Plant Physiol. 140: 922-932.

(Continued)

*Primary Examiner*—Medina A Ibrahim
(74) *Attorney, Agent, or Firm*—Saliwanchik, Lloyd & Saliwanchik

(57) ABSTRACT

Methods of using genetically-transformed plants in the phytoremediation of lead are described. Unlike many organisms in which only 10-kDa ACBPs have been identified, there exists a family of six ACBPs in the model plant *Arabidopsis*. Other than a function in mediating the transfer of acyl-CoA esters in plant lipid metabolism, all six *Arabidopsis* ACBPs can bind the heavy metal lead and are therefore applicable for phytoremediation. These methods of phytoremediation will provide a cheap, simple and efficient method in the removal of contaminating lead from soil/water/environment by the growth of the ACBP-overexpressing genetically-transformed plants in the contaminated environment. There is also provided a method to remove lead from contaminated water.

21 Claims, 12 Drawing Sheets

OTHER PUBLICATIONS

Kragelund et al. 1999. Acyl-coenzyme A binding protein (ACBP). Biochim. Biophy. Acta 1441: 150-161.

Kramer, Ute. 2005. Phytoremediation: novel approaches to cleaning up polluted soils. Curr. Opin. Biotech. 16: 133-141.

Laemmli, U.K. 1970. Cleavage of structural proteins during the assembly of the head of bacteriophage T4. Nature 227: 680-685.

Layne, Ennis. 1957. Spectrophotometric and turbidimetric methods for measuring protein. Methods in Enzymology 3: 447-454.

Lee et al. 2005. AtPDR12 contributes to lead resistance in Arabidopsis. Plant Physiol. 138: 827-836.

Leung et al. 2004. ACBP4 and ACBP5, novel Arabidopsis acyl-CoA-binding proteins with kelch motifs that bind oleoyl-CoA. Plant Mol. Biol. 55: 297-309.

Leung et al. 2006. Arabidopsis ACBP3 is an extracellularly targeted acyl-CoA-binding protein. Planta 223: 871-881.

Li, Hong-Ye and Chye, Mee-Len, 2003. Membrane localization of Arabidopsis acyl-CoA-binding protein ACBP2. Plant Mol. Biol. 51: 483-492.

Li et al. 2006. Accumulation of recombinant SARS-CoV spike protein in plant cytosol and chloroplasts indicate potential for development of plant-derived oral vaccines. Exp. Biol. Med. 231: 1346-1352.

Murashige, Toshio and Skoog, Folke. 1962. A revised medium for rapid growth and bio assays with tobacco tissue cultures. Physiol. Plant. 15: 473-497.

Needleman, Saul B. and Wunsch, Christian D. 1970. A general method applicable to the search for similarities in the amino acid sequence of two proteins. J. Mol. Biol. 48: 443-453.

Nitz et al. 2005. Identification of new acyl-CoA-binding protein transcripts in human and mouse. Int. J. Biochem. Cell Biol. 37: 2395-2405.

Powell, K. 2002. Genes improve green cleaning. Nature doi: 10.1038/news021001-14.

Rasmussen et al. 1990. Comparison of the binding affinities of acyl-CoA-binding protein and fatty-acid-binding protein for long-chain acyl-CoA esters. Biochem. J. 265: 849-855.

Rogers et al. 1988. Use of cointegrating Ti plasmid vectors. In Gelvin SB, Schilperoort RA and Verma DPS. (eds.) Plant Molecular Biology Manual pp. A2: 1-12. Kluwer Academic Publishers.

Shi et al. 2005. SLOW WALKER1, essential for gametogenesis in Arabidopsis, encodes a WD40 protein involved in 18S ribosomal RNA biogenesis. Plant Cell 17:2340-2354.

Shpaer Eugene G. 1997. GeneAssist. Smith-Waterman and other database similarity searches and identification of motifs. Meth. Mol. Biol. 70: 173-187. (First page only).

Sivanandan et al. 2005. T-DNA tagging and characterization of a cryptic root-specific promoter in Arabidopsis. Biochimica et Biophysica Acta 1731:202-208.

Smith et al. 1998. High-affinity renal lead-binding proteins in environmentally-exposed humans. Chem. Biol. Interact. 115: 39-52.

Song et al. 2003. Engineering tolerance and accumulation of lead and cadmium in transgenic plants. Nat. Biotech. 21(8): 914-919.

Staub, Jeffrey M. and Maliga, Pal. 1994. Translation of Psba mRna Is Regulated by Light Via the 5'-Untranslated Region in Tobacco Plastids. Plant J. 6(4): 547-553.

Stemmer, Willem P.C. 1994. DNA shuffling by random fragmentation and reassembly: in vitro recombination for molecular evolution. Proc. Natl. Acad. Sci. USA. 91: 10747-10751.

Stemple, Derek L. 2004. TILLING-a high-throughput harvest for functional genomics. Nature Reviews, 5: 1-7.

Suzuki et al. 2003. Unique architecture of the plastid ribosomal RNA operon promoter recognized by the multisubunit RNA polymerase in tobacco and other higher plants. Plant Cell 15: 195-205.

Swinnen et al. 1996. A human gene encoding diazepam-binding inhibitor/acyl-CoA-binding protein:transcription and hormonal regulation in the androgen-sensitive human prostatic adenocarcinoma cell line LNCaP. DNA Cell Biol. 15: 197-208.

Xiao et al. 2004. COS1: an Arabidopsis coronatine insensitive1 suppressor essential for regulation of jasmonate-mediated plant defense and senescence. Plant Cell 16: 1132-1142.

* cited by examiner

```
ACBP6   1   MGLKEEFEEHAEKVNT- --------LTELPSN EDLLILYGLYKQAKF GPVDTSRPGMFSMKE  52
ACBP1  94   --.D.A.SAATAF.AAA ASD----RLSQKVSN ELQLQ......I.TE ..CTAPQ.SALK.TA 149
ACBP2 104   --.D.A.SAATLF.TTA AAD----RLSQKVPS DVQQQ......I.TE ..CTAPQ.SALK.TA 160
ACBP3 231   --.EKA.AAA---.NLL EES----GKAEEIGA EAKME.F..H.I.TE .SCREAQ.MAVMISA 283
ACBP4  12   --YP.R.YAAASY.GLD GSDSSAKNVISKFPD DTALL..A..QQ.TV ..CNTPK.SAWRPV.  71
ACBP5  22   --YP.R.YAAASY.GLD GSQSSVKQLSSKFSN DTSLL..T.HQQ.TL ..CSIPK.SAWNPV.  72
Con             F A  V                              L L  T  G C     P A
Com         LDEAFSAAASFVGLA ASDSS KRLSSKVSN DTQLQLYGLYKIATE GPCTAPQPSALKMTA
             YP R Y  T Y  D  G           Q FP E   L      HQQ        K  W PVE

ACBP6  53   RAKWDAWKAVEGKSS EEAMNDYITKVKQLL EVAASKAST          92
ACBP1 150   ....Q..QKLGAMPP ....EK..DL.T..Y P-                180
ACBP2 161   ....Q..QKLGAMPP ....EK..EI.T..Y P-                190
ACBP3 284   ....N..QKLGNM.Q ....EQ.LAL.SKEI PG                315
ACBP4  72   QS..KS.QGLGTMP. I...RLFVKILEEDD PG                103
ACBP5  73   QS..KS.QGLGTMP. I...RLFVKILEEAD PG                104
Con         KW  WQ  G M      EAM           P
Com         RAKWQAWQKLGAMPP EEAMEKYIKIVTQLY PG
            QS  KS  G  T  S I    RLFV LLEE D
```

FIG. 2D

FIG. 3A

FIG. 3B

METHODS OF USING TRANSFORMED PLANTS EXPRESSING PLANT-DERIVED ACYL-COENZYME-A-BINDING PROTEINS IN PHYTOREMEDIATION

CROSS-REFERENCE TO RELATED APPLICATION

This application claims the benefit of U.S. provisional application Ser. No. 60/922,847, filed Apr. 11, 2007.

TECHNICAL FIELD

The present invention relates generally to a method of bioremediation, and more specifically to using genetically-transformed plants for phytoremediation of lead and other metal pollutants.

BACKGROUND OF THE INVENTION

Phytoremediation is the process by which plants are used to remove pollutants like heavy metals from the environment. The roots of the plant "suck up" the pollutants from the environment and these can be stored within the plant. Plants thrive by photosynthesis, hence phytoremediation is solar-driven, environmentally-friendly, low-cost and remediation occurs in situ.

Heavy metals, the undesirable products from industries like mining and manufacturing, as well as agriculture, contaminate the environment by polluting streams, sediment, sludge, groundwater, and soil. Transgenic plants have been successfully used to detoxify heavy metals like mercury, cadmium, arsenate, and selenate from soil (Kramer, *Curr. Opin. Biotech.* 16: 133-141, 2005). Such heavy metals, toxic to humans and animals, adversely affect the human nervous system and induce cancers. These pollutants are also known to stress the growth and development of wild-type plants growing on contaminated soils. Transgenic plants that contain heterologous gene(s), with the ability to "detoxify" the pollutant, can tolerate the heavy metal stress and will concurrently clean-up the environment. The toxin will be absorbed and concentrated in the plant tissue such as in leaves and stems. Subsequently, these plants (if the toxin is yet not degraded) can be harvested and then incinerated safely. This is especially applicable to metal pollutants including arsenate, cadmium, and mercury which cannot be easily broken down (Powell, *Nature* doi: 10.1038/news021100-14, 2002).

Genetic engineering has made it possible to transfer non-plant derived genes for expression in plants. Examples in phytoremediation of genetically-transformed plants expressing non-plant genes include those that express bacterial enzymes that breakdown arsenic compounds in transgenic *Arabidopsis* (Dhankher et al., *Nature Biotech.* 20: 1140-1146, 2002) and others that detoxify mercury (Kramer, *Curr. Opin. Biotech.* 16: 133-141, 2005). The generation of transgenic *Arabidopsis* and *Brassica* plants that detoxify selenate has also been reported (Kramer, *Curr. Opin. Biotech.* 16: 133-141, 2005).

There is an apparent lack of plant genes that encode proteins capable of binding lead. Transgenic plants that can potentially phytoremediate lead have been generated by the expression of a yeast YCF1 protein (Song et al., *Nature Biotech.* 21: 914-919, 2003). Bacterial P-type ATPases which remove lead are deemed unsuitable for phytoremediation because their use will not culminate in the accumulation of lead in plants cells (Song et al., *Nature Biotech.* 21: 914-919, 2003). Since lead toxicity is of prime concern to human health, particularly that of children, phytoremediation would provide a useful strategy to eliminate lead accumulation and its concentration in food chains. Hence, such procedures in lead bioremediation are invaluable for the protection of human health and the environment worldwide.

It has been previously reported that two low molecular weight cytosolic proteins isolated from human kidney tissue have been observed to bind physiologic lead in vivo with high affinities. The two human proteins were identified as thymosin beta-4 of molecular mass 5 kDa and a 9-kDa acyl-CoA-binding protein (Smith et al., *Chemico-Biological Interactions* 115: 39-52, 1998). These small proteins, known to be highly-conserved in mammals, have been suggested to be the specific molecular targets for lead in environmentally-exposed humans (Smith et al., *Chemico-Biological Interactions* 115: 39-52, 1998).

The 9-kDa human ACBP is homologous to the bovine 10-kDa cytosolic ACBP (diazepam-binding inhibitor/enzepine), and such 10-kDa ACBPs have already been well-characterized in many organisms (reviewed in Kragelund et al., *Biochim Biophys Acta* 1441: 150-161, 1999) including man (Swinnen et al., *DNA Cell Biol.* 15: 197-208, 1996). Bovine 10-kDa ACBP and rat 10-kDa ACBP have been demonstrated to bind palmitoyl-CoA and oleoyl-CoA (Rasmussen et al., *Biochem. J.* 265: 849-855, 1990). The 10-kDa ACBP has been implicated to mediate intracellular acyl-CoA transport by binding long-chain acyl-CoA esters (reviewed in Kragelund et al., *Biochim Biophys Acta* 1441: 150-161, 1999). These long-chain acyl-CoAs esters not only function as intermediates in lipid metabolism but have been implicated in protein trafficking, vesicular trafficking, and gene regulation (reviewed in Faergman and Knudsen, *Biochem. J.* 323: 1-12, 1997).

In the model plant *Arabidopsis*, a 10-kDa ACBP (GenBank Accession No. NP_174462) that is homologous to the previously characterised human and bovine ACBPs, has been reported by Engeseth et al. (*Arch. Biochem. Biophys.* 331: 55-62, 1996). However, our recent work has shown that other forms of ACBPs are also known to occur in *Arabidopsis* (Leung et al., *Plant Mol. Biol.* 55: 297-309, 2004). The *Arabidopsis* complete ACBP gene family of six members encode proteins ranging from 92 amino acids to 668 amino acids, each containing a conserved acyl-CoA-binding domain (Leung et al., *Plant Mol. Biol.* 55: 297-309, 2004). Specifically, they are the *Arabidopsis* ACBP6 (SEQ ID NO: 26) (10-kDa ACBP, GenBank Accession No. NP_174462, Engeseth et al., *Arch. Biochem. Biophys.* 331: 55-62, 1996), membrane-associated ACBP1 (SEQ ID NO: 27) (GenBank Accession No. AAD03482, Chye et al., *Plant J.* 18: 205-214, 1999), membrane-associated ACBP2 (SEQ ID NO: 28) (GenBank Accession No. NP_194507, Chye et al., *Plant Mol. Biol.* 44: 711-721, 2000; Li and Chye, *Plant Mol. Biol.* 51: 483-492, 2003), ACBP3 (SEQ ID NO: 29) (GenBank Accession No. NP_194154, Leung et al., *Planta* 223: 871-881, 2006) and the two kelch-motif-containing ACBPs, ACBP4 (SEQ ID NO: 30) (GenBank Accession No. NP_187193, Leung et al., *Plant Mol. Biol.* 55: 297-309, 2004) and ACBP5 (SEQ ID NO: 31) (GenBank Accession No. NP_198115, Leung et al., *Plant Mol. Biol.* 55: 297-309, 2004).

Many ACBPs identified in other organisms are 10-kDa homologs of the 10-kDa bovine ACBP, consisting of 86-104 amino acids, or variants thereof arising from alternative first exon usage (Nitz et al., *Int. J. Biochem. Cell Biol.* 37: 2395-2405, 2005). The membrane-associated domains of *Arabidopsis* ACBP1 (consisting of 338 amino acids) and ACBP2 (consisting of 354 amino acids) are located at the N-terminus and both have C-terminal ankyrin repeats. ACBP1 and ACBP2 share 76.9% amino acid identity. Highly-conserved (81.4% identity) ACBP4 and ACBP5 both contain C-terminal kelch motifs. Ankyrin repeats and kelch motifs are domains that can potentially mediate protein-protein interactions, suggesting these *Arabidopsis* ACBPs can interact with protein partners (Leung et al., *Plant Mol. Biol.* 55: 297-309, 2004).

Thus, according to presence of structural domains, the *Arabidopsis* ACBP family can be divided into four classes: (1) small 10-kDa ACBP6 of 92 amino acids; (2) ACBP1 (338 amino acids) and ACBP2 (354 amino acids) with N-terminal membrane-associated domains and C-terminal ankyrin repeats; (3) ACBP3 of 362 amino acids; and (4) kelch-motif containing large ACBP4 (668 amino acids) and ACBP5 (648 amino acids). To establish the significance of each acyl-CoA-binding domain in binding acyl-CoA esters, *Arabidopsis* ACBPs have been expressed as recombinant (His)-tagged proteins in *Escherichia coli* for in vitro binding assays, and residues within the acyl-CoA-binding domain essential in binding have been identified by site-directed mutagenesis (Chye et al., *Plant Mol. Biol.* 44: 711-721, 2000; Leung et al., *Plant Mol. Biol.* 55: 297-309, 2004; Leung et al., *Planta* 223: 871-881, 2006). The differential binding affinities of *Arabidopsis* ACBPs to various acyl-CoA esters suggest they may possess different cellular functions.

Since the expression of plant-derived gene(s) in transformed plants may generally be more acceptable to the public, we provide herein below a method for the phytoremediation of lead and other metals by the expression or overexpression of plant-derived acyl-CoA-binding proteins (ACBPs) in transformed plants.

BRIEF SUMMARY OF THE INVENTION

An aspect of the present invention is based on the observation that genetically modified plants and progeny thereof expressing acyl-CoA-binding proteins (ACBP) can be applied for phytoremediation of heavy metals like lead (Pb (II)). Presented herein are plant transformation vectors that each comprises a nucleic acid sequence encoding an ACBP that can be used to generate genetically-transformed plants via nuclear transformation or plastid transformation. The resultant plants that overexpress ACBPs, exemplified herein by *Arabidopsis* ACBPs, are conferred the ability to grow in an environment that contains a heavy metal pollutant, for example, lead, copper, and cadmium. These plants are able to uptake such metals and incorporate them in their tissue, and hence are useful for the phytoremediation of lead and other metals.

Since all six Acyl-Coenzyme-A-Binding Proteins (ACBPs) from *Arabidopsis* can bind the heavy metal lead, and other metal contaminants present as divalent cations (such as, for example, copper and cadmium), growth of genetically-transformed plants overexpressing these ACBPs will absorb such contaminants from the environment. The plants can subsequently be harvested, thereby removing the contaminant. In specific embodiments, the generation of transgenic plants overexpressing *Arabidopsis* ACBPs from plant transformation vectors is described.

In accordance with another aspect of the present invention, there are provided plant transformation vectors comprising polynucleotides which encode fragments, derivatives, analogs, or variants of ACBP polypeptides. In specific embodiments, the invention provides for transformed plants such as transgenic *Arabidopsis* and transplastomic tobacco plants. The present invention provides modified plants that comprise ACBP polypeptides or fragments, derivatives, analogs, or variants thereof having similar activities as the ACBP polypeptides. The present invention also provides a method of producing the modified plants which comprises transforming a plant with a plastid and/or nuclear transformation vector comprising at least one ACBP-encoding polynucleotide, or fragments, derivatives, analogs, or variants thereof.

In another specific embodiment, plant transformation vectors are engineered to yield plants that can be used to phytoremediate heavy metals, particularly those present as divalent cations such as lead, from contaminated soil/water environments. One aspect of the invention relates to methods of detecting Pb(II) in a sample by growth of *Arabidopsis* test plants and detection of lead Pb(II) by observation in the mRNA induction of mRNAs encoding ACBP 1 to ACBP5. The sample may be a liquid or solid (e.g. soil) from the environment.

In one specific embodiment, the invention provides for a plastid transformation vector comprising at least one polynucleotide encoding an ACBP, or encoding a fragment, derivative, analog, or variant of an ACBP. In another specific embodiment, the invention provides for a nuclear transformation vector comprising at least one polynucleotide encoding an ACBP, or encoding a fragment, derivative, analog, or variant thereof. In another embodiment, the invention provides for a nuclear transformation vector which expresses at least one ACBP polypeptide, or a fragment, derivative, analog, or variant thereof, having a similar lead-binding activity as the ACBP polypeptide. In a specific embodiment, the present invention provides a method of producing transgenic plants via the exemplary nuclear transformation vectors pAT31 and pAT314.

Plant cells containing a vector comprising a polynucleotide encoding a polypeptide exhibiting ACBP activity are also an aspect of this invention. Plant parts of the modified plants, such as for example, fruits, leaves, tubers, seeds, flowers, stems or roots, which comprise cells expressing ACBP polypeptides, derivatives, analogs, or variants thereof are provided in the invention. The plant parts include parts that are separated from the whole plant or attached onto the whole plant.

In a specific embodiment, a nuclear transformation vector is used to cause expression of one or more ACBPs including ACBP polypeptides or fragments, derivatives, analogs, or variants thereof having similar lead-binding activities as the *Arabidopsis* ACBP polypeptides. In a specific embodiment, a plastid transformation vector is used to cause expression of one or more ACBPs including ACBP polypeptides or fragments, derivatives, analogs, or variants thereof having similar lead-binding activities as the *Arabidopsis* ACBP polypeptides. In a specific embodiment, the present invention provides a method of producing transgenic plants via the exemplary plastid transformation vector pAT385. In a specific embodiment, a plastid transformation vector and a nuclear transformation vector are used to express one or more ACBPs, including ACBP polypeptides, or fragments, derivatives, analogs, or variants thereof having similar lead-binding activities as the ACBP polypeptides. Such nuclear and plastid transformation vectors can be used alone or in conjunction with other recombinant vectors that can enhance the phytoremediation capabilities of plants transformed therewith.

The present invention provides a method of producing ACBPs in plants, or fragments, derivatives, analogs, or variants thereof having similar lead-binding activities as the ACBP polypeptides. The method comprises transforming a plant with a vector which comprises a polynucleotide coding for one or more ACBP polypeptides. The vector can optionally also comprise a promoter, operably linked to the coding sequence, and a terminator, and/or other regulatory elements.

The vector can be designed to introduce the heterologous polypeptide so that it will be expressed under the control of a plant's own endogenous promoter, such as, for example, in the pseudogene technique taught by Hahn and Kuehnle (US 2003-003362641). Alternatively, or in addition, the vector can contain a constitutive and/or inducible and/or tissue specific promoter operatively linked to the ACBP-encoding polypeptide. Plant cells containing a vector which comprises one or more nucleic acid sequences encoding ACBPs, including polypeptides or fragments, derivatives, analogs, or variants thereof having the similar lead-binding activities as the ACBP polypeptides are also an aspect of this invention. Alternatively, the plant cells may contain one or more vectors of the present invention. Each vector may contain an exogenous polypeptide encoding one polypeptide exhibiting the lead-binding activity of an ACBP, or optionally may contain an operon encoding more than one such ACBP polypeptide. The present invention provides plant parts, such as for example, fruits, leaves, tubers, seeds, flowers, stems, roots, and all other anatomical parts of the modified plant.

The *Arabidopsis* ACBP proteins were first tested for binding lead using recombinant His-tagged proteins expressed in *E. Coli* to mass-produce and facilitate the purification of the His-tagged ACBPs for in vitro lead-binding assays, because isolation of the native forms from *Arabidopsis* is more difficult to achieve and to mass-accumulate for in vitro assays. Subsequently, we demonstrated that in vitro translated ACBP2 also binds copper and cadmium, thus providing the expectation that the ACBPs taught herein are useful for binding not only lead, copper, and cadmium, but other metals present as divalent cations.

Upon demonstration of the abilities of all six *Arabidopsis* ACBPs in binding lead using lead-binding assays, we next investigated if the overexpression of an ACBP in a transgenic plant would confer tolerance to lead in the plant growth medium. Plasmid constructs containing nucleic acids that encode ACBPs were generated for plant transformation. Subsequently, the growth of ACBP-overexpressing transgenic lines was compared to wild-type *Arabidopsis*. The ACBP-overexpressing lines showed better growth in medium containing lead than wild type, indicating that ACBP confers the ability to bind lead and tolerate the presence of lead in the growth environment. The introduction of an ACBP transgene in the transformed plant provided the plant a higher tolerance to lead stress in the growth environment.

To confirm that these ACBP overexpressing plants can phytoremediate lead from the environment, the concentration of lead in shoots and roots of these plants was determined and compared with wild type growing on the lead-containing medium. Results demonstrate that the ACBP-overexpressing plants accumulate lead in their shoots, thus indicating they can phytoremediate lead from the environment, and providing the expectation that they can phytoremediate other metals present in the environment as divalent cations.

Figure 1:
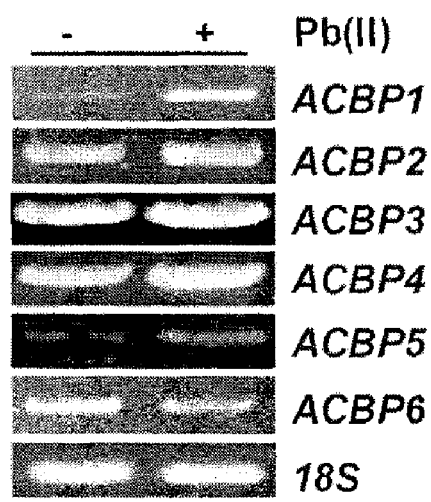
FIG. 1 shows Reverse-Transcription Polymerase Chain Reaction (RT-PCR) analysis of lead Pb(II)-induced elevation of *Arabidopsis* ACBP transcripts (ACBP1 to ACBP5 but not ACBP6) in root. Total RNA was extracted from roots of 3-week-old Col-0 *Arabidopsis* seedlings in the presence (+) or absence (−) of 1 mM $Pb(NO_3)_2$ treatment under continuous light for 24 h. The 18S rDNA transcript was used as a loading control (bottom of figure).

Primers used for RT-PCR analysis of ACBP6 were ML750 (SEQ ID NO:1) and ML751 (SEQ ID NO:2); ACBP1, ML179 (SEQ ID NO:3) and ML759 (SEQ ID NO:4); ACBP2, ML194 (SEQ ID NO:5) and ML205 (SEQ ID NO:6); ACBP3, ML783 (SEQ ID NO:7) and ML784 (SEQ ID NO:8); ACBP4, ML849 (SEQ ID NO:9) and ML850 (SEQ ID NO:10); ACBP5, ML352 (SEQ ID NO:11) and ML353 (SEQ ID NO:12); 18S, 18S-F (SEQ ID NO:13) and 18S-R (SEQ ID NO:14).

FIGS. 2A-2D compares binding of $(His)_6$-ACBPs and in vitro translated ACBPs to Pb(II), Cd(II), and Cu(II). (A) Binding of $(His)_6$-ACBPs to Pb(II) by fluorescence analysis. The fluorescence intensities were measured with excitation wavelength set at 360/40 nm and emission wavelength set at 530/25 nm n for the dansylated $(His)_6$-ACBP in the absence and presence of various concentrations (1, 2, 3, 4, 5, 7, and 9 μM) of Pb(II). The relative fluorescence of each ACBP was obtained by deduction of its own blank. The maximum value for relative fluorescence was set at 1 against which others were then compared to obtain the percentage relative fluorescence. Each point shows the average and standard error of three independent experiments. Bars represent SE (n=3). (B) Binding of in vitro translated ACBPs to Pb(II) by metal-chelate affinity chromatography. The left panel (Input) shows equal loadings of [$^{35}$S]methionine-labeled ACBP1, ACBP2, and ACBP6. The right panel shows in vitro binding between radiolabeled proteins and Pb(II). Pb(II)-equilibrated matrix was incubated with [$^{35}$S]methionine-labeled proteins, washed 3 times and the binding protein was eluted with an imidazole elution buffer followed by extraction with 2% SDS, 50 mM DTT. The eluted protein was analyzed by SDS-PAGE followed by autoradiography. (C) Binding of in vitro translated ACBPs to Pb(II), Cd(II), and Cu(II) by metal-chelate affinity chromatography. The first panel on the left (Input) shows equal loadings of [$^{35}$S]methionine-labeled ACBP2 and ACBP6. The next panels show in vitro binding between radiolabeled proteins and heavy metals as indicated. Pb(II), Cd(II), or Cu(II)-equilibrated matrix was incubated with [$^{35}$S]methionine-labeled proteins, washed 3 times and the binding protein was eluted with an imidazole elution buffer followed by extraction with 2% SDS, 50 mM DTT. The eluted protein was analyzed by SDS-PAGE followed by autoradiography. Binding of ACBP2 to Pb(II), Cd(II), and Cu(II) was inhibited by the metal chelator, ethylenediaminetetraacetic acid (EDTA at 50 mM final concentration), indicating that binding is dependent on divalent cations. (D) Comparison of the acyl-CoA-binding domains of *Arabidopsis* ACBPs. Dots indicate identity to ACBP6. "Con" (Conserved), amino acid residues highly conserved in *Arabidopsis* ACBPs. All *Arabidopsis* ACBPs (ACBP1 to ACBP6) show 100% conservation in 13 amino acid residues (marked with asterisks in "Con" sequence in FIG. 2D). Ten other amino acid residues (underlined amino acids in "Con" sequence in FIG. 2D) within the acyl-CoA-binding domain, are conserved in ACBP1 to ACBP5, but not in ACBP6. From these 10 (underlined amino acids in "Con"), 3 amino acid residues that are further conserved in the 9-kDa human ACBP (GenBank Accesssion No. NM_020548) are encircled; these 3 amino acid residues conserved in human ACBP and ACBP1 to ACBP5 may play an important role in binding (Pb(II). Below "Con", the "Com" (Common) amino acids that are common in ACBPs are displayed. "Com" lists the amino acids within the acyl-CoA-binding domains of ACBP1 to ACBP5 that are common in at least 2 of these 5 ACBPs (ACBP1 to ACBP5). At positions in which 2 different residues occur in 2 or more ACBPs, both are shown, with one below the other.

FIGS. 3A-3B show construction of pAT31 (35S::ACBP1) and pAT314 (35S::ACBP3-GFP) plant transformation vectors. (A) Construct of 35S:ACBP1 in plasmid pAT31 in which the ACBP1 cDNA is expressed from the Cauliflower Mosaic Virus (CaMV) 35S promoter. The ACBP1 full-length cDNA was cloned in the SmaI site of binary vector pBI121 (Clontech). This pBI121 derivative was used in the generation of ACBP1-overexpressing *Arabidopsis* plants. (B) Construct of 35S:ACBP3-GFP in plasmid pAT314. The ACBP3 full-length cDNA was cloned into BamHI site of binary vector pBI-GFP which is a pBI121 derivative obtained by replacement of the GUS gene in pBI121 with eGFP (Shi et al., *Plant Cell* 17: 2340-2354, 2005). ACBP3 is translationally fused with GFP and expressed from Cauliflower Mosaic Virus (CaMV) 35S promoter. The primer 35SB (designated SEQ ID NO:15) used to genotype transformed plants is located within the CaMV 35S promoter region.

Figure 4A:
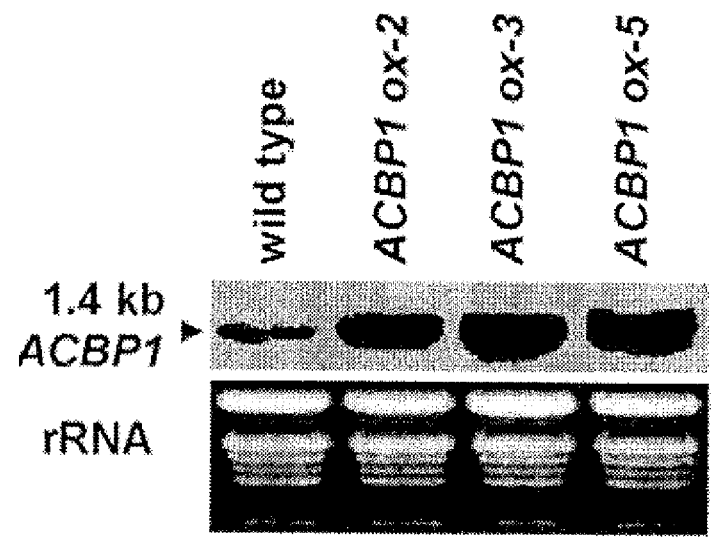
Figure 4B:
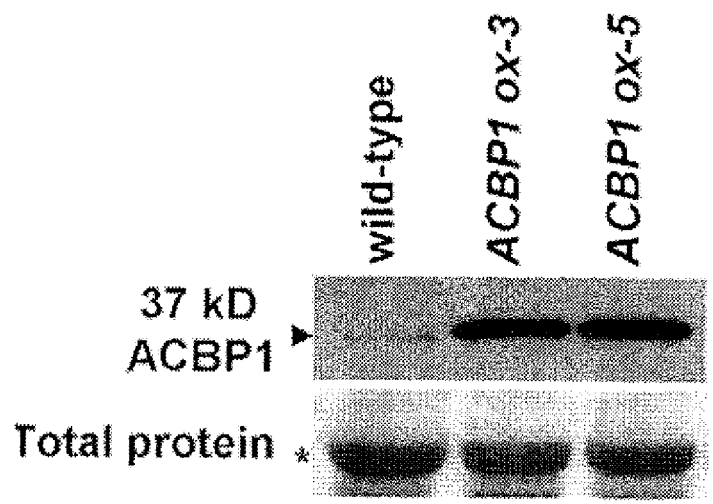
Figure 4C:
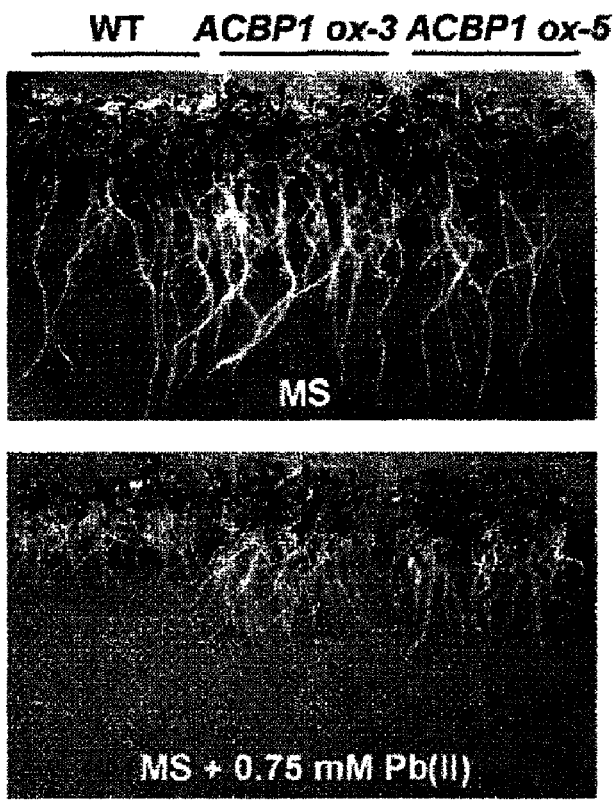
Figure 4D:
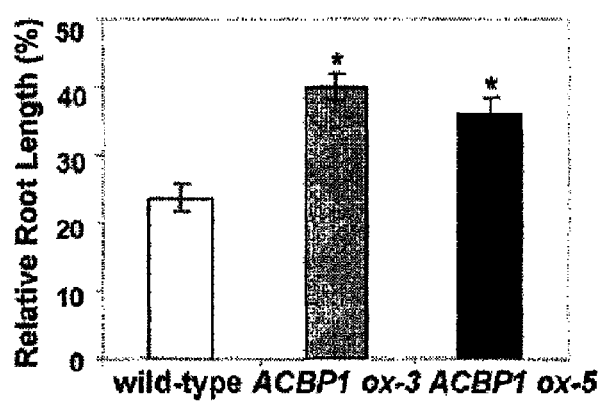
Figure 4E:
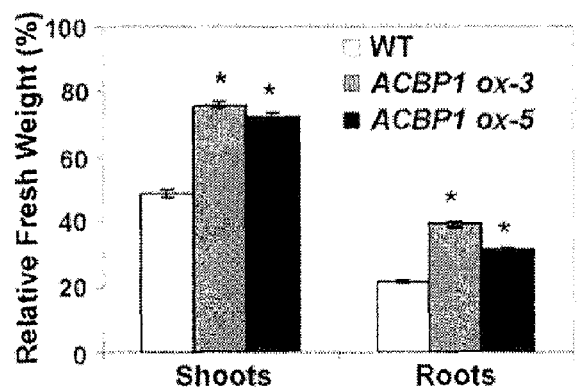

FIGS. 4A-4E show analyses on ACBP1-overexpressing *Arabidopsis* plants and their improved tolerance to Pb(II) stress. (A) RNA gel blot analysis of ACBP1 transcript levels in wild-type *Arabidopsis* (Col-0) and 3 independent ACBP1-overexpressing *Arabidopsis* transgenic lines: ACBP1 ox-2, ox-3 and ox-5 using an ACBP1 cDNA probe. Ethidium bromide-stained rRNA is shown below the blots to indicate the relative amounts of total RNA loaded. (B) Western blot analysis of ACBP1 protein levels in wild-type *Arabidopsis* (Col-0) and ACBP1-overexpressing *Arabidopsis* transgenic lines ACBP1 ox-3 and ACBP1 ox-5 using ACBP1-specific antibodies (Chye, *Plant Mol. Biol.* 38: 827-838, 1998). Bottom, gel identically loaded stained with Coomassie Blue shows the 54-kDa band of RuBisCO large subunit (asterisk). (C) Phenotype of 2-week-old wild-type (Col-0), ACBP1 ox-3 and ACBP1 ox-5 seedlings grown in MS medium and MS medium containing 0.75 mM Pb(NO$_3$)$_2$. (D) Comparison in relative root length of *Arabidopsis* plants grown in MS medium containing 0.75 mM Pb(NO$_3$)$_2$ as shown in FIG. 4C. Bars represent SE (n=10). *P<0.05 by Student's t-test. (E) Comparison in relative fresh weights of shoots and roots of *Arabidopsis* plants grown in MS medium containing 0.75 mM Pb(NO$_3$)$_2$ as shown in FIG. 4C. Bars represent SE (n=10). Roots lengths and fresh weights were expressed relative to the values obtained from seedlings grown on MS (100%). *P<0.05 by Student's t-test.

Figure 5A:
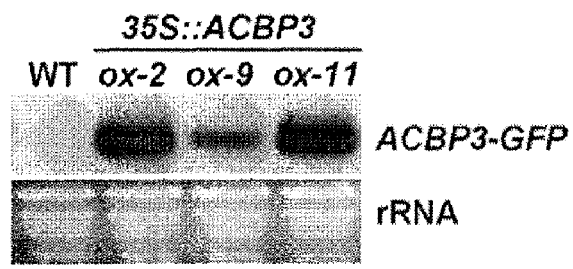
Figure 5B:
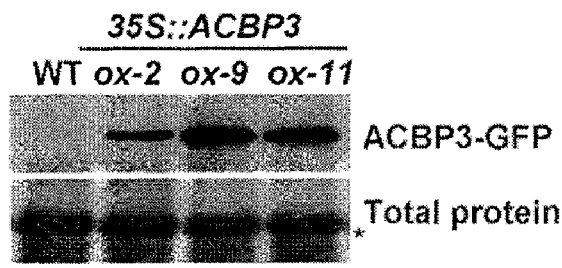
Figure 5C:
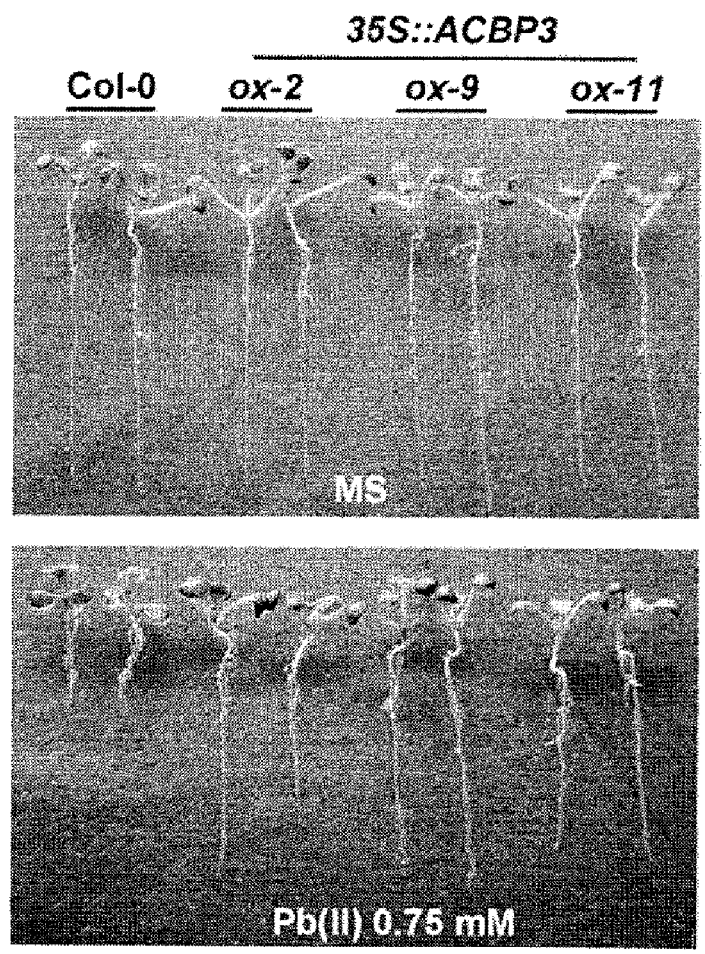
Figure 5D:
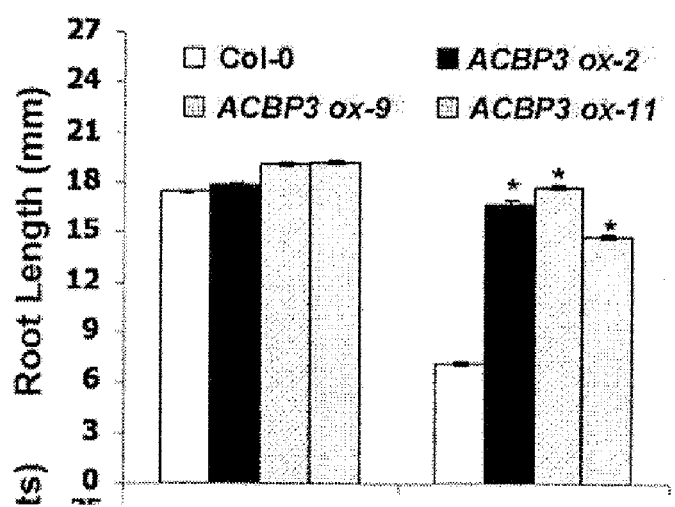

FIGS. 5A-5E show analyses on ACBP3-overexpressing *Arabidopsis* plants and their enhanced tolerance to Pb(II) treatment. (A) RNA gel blot analysis of ACBP3-GFP transcript levels in wild type (Col-0) and 3 independent ACBP3-overexpressing *Arabidopsis* transgenic lines ACBP3 ox-2, ox-9, and ox-11. Ethidium bromide-stained rRNA is shown below the blots to indicate the relative amounts of total RNA loaded. (B) Western blot analysis of ACBP3-GFP fusion protein levels in wild-type *Arabidopsis* (Col-0) and ACBP3-overexpressing *Arabidopsis* transgenic lines ACBP3 ox-2, ACBP3 ox-9, and ACBP3 ox-11 using the GFP-specific antibodies. Bottom, gel identically loaded stained with Coomassie Blue shows the 54-kDa band of RuBisCO large subunit (asterisk). (C) Three-week-old wild-type (Col-0) and transgenic (ACBP3 ox-2, ACBP3 ox-9, and ACBP3 ox-11) seedlings grown in MS medium and MS medium containing 0.75 mM Pb(NO$_3$)$_2$. (D) Root length analysis of the plants grown in MS medium in the presence and absence of Pb(II) as depicted in FIG. 5C. (E) Fresh weight analysis of the plants grown in MS in the presence and absence of Pb(II), as depicted in FIG. 5C. Bars represent SE (n>10). *P<0.05 by Student's t-test.

Figure 6A:
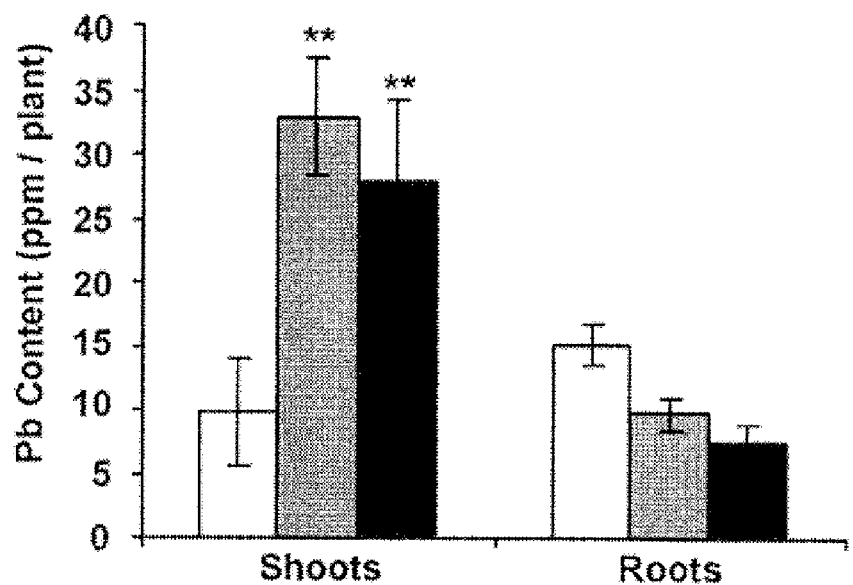
Figure 6B:
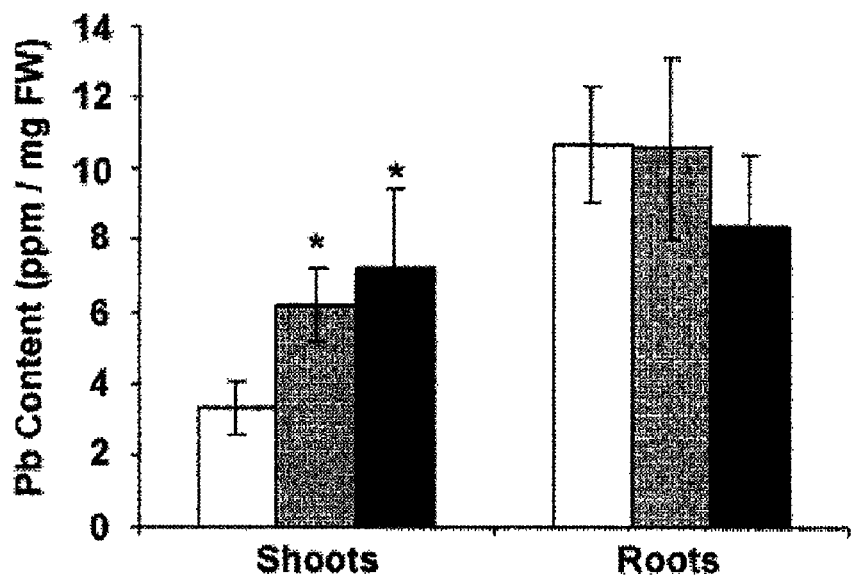

FIGS. 6A and 6B show Pb(II) contents in wild-type *Arabidopsis* (Col-0) and in transgenic *Arabidopsis*, ACBP1 ox-3 and ACBP1 ox-5. *Arabidopsis* plants were grown on MS medium for 2 to 3 weeks and then transferred into 1 mM Pb(NO$_3$)$_2$ solution for 48 h. The shoots and roots were collected for Pb(II) content measurement. Samples were digested overnight at 200° C. with 11 N HNO$_3$. After dilution with 0.5 N HNO$_3$ according to Lee et al. (*Plant Physiol.* 138: 827-836, 2005), the samples were analyzed using an atomic absorption spectrometer (PERKIN ELMER-AA Spectrometer 3110). Six replicates were tested for each plant line and each replicate contains 5 plants. The Pb(II) contents were normalized on either a per-plant basis (FIG. 6A) or a per fresh weight basis (FIG. 6B) and the significant difference of ACBP1 ox-3 and ACBP1 ox-5 from wild type was determined by Student's t-test (*P<0.05, **P<0.001). Bars represent SE (n=30).

Figure 7A:
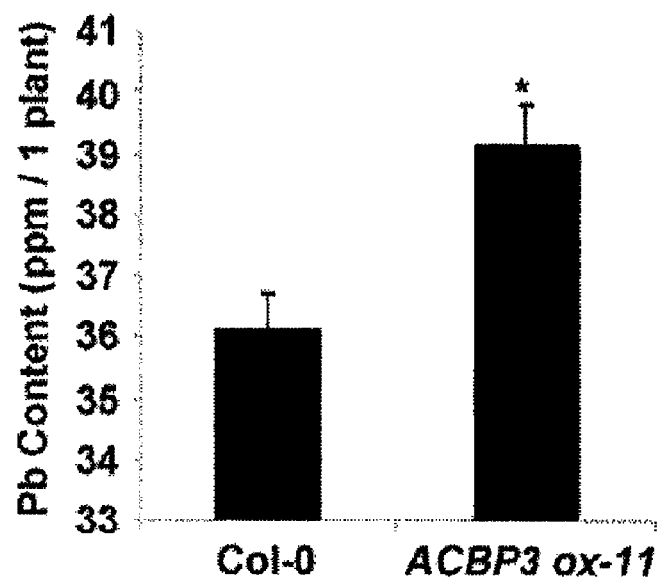
Figure 7B:
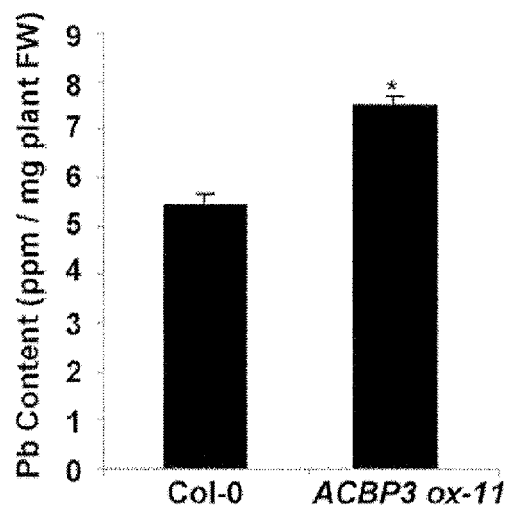

FIGS. 7A and 7B show comparison in Pb(II) content between wild-type *Arabidopsis* (Col-0) and *Arabidopsis* transgenic line ACBP3 ox-11. Six replicates were tested for each plant line and each replicate contains 5 plants. Pb(II) content was normalized on either a per-plant basis (FIG. 7A) or a per-fresh weight basis (FIG. 7B). The significant difference between ACBP3 ox-11 and wild type was determined by using the Student's t-test (*P<0.05). Bars represent SE (n=30).

Figure 8A:
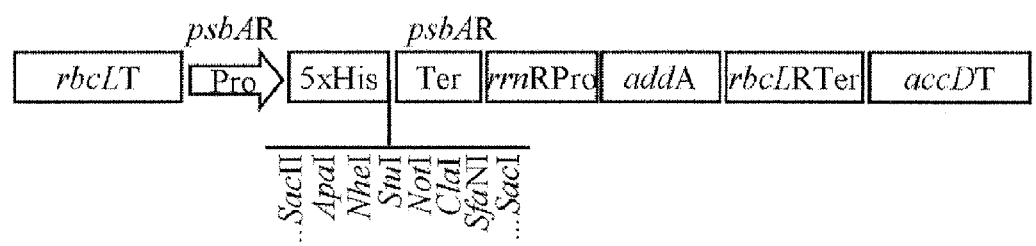
Figure 8B:
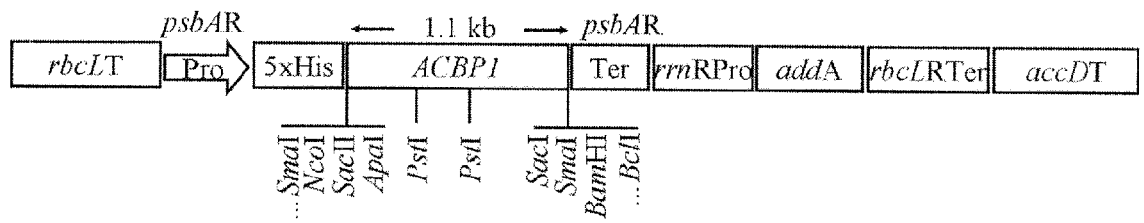

FIG. 8 shows restriction map of plastid transformation vector pAT385. The 1.1-kb ACBP1 cDNA fragment was generated by RT-PCR using primer pairs ML916 (SEQ ID NO:16) and ML917 (SEQ ID NO:17) and was cloned in pGEM-T EASY vector (Promega). The ACBP1 fragment was then obtained by digestion with restriction enzymes ApaI and SacI and was subsequently inserted into the ApaI-SacI sites of plastid transformation vector pMLV-HisA (FIG. 8A; Li et al. *Exp. Biol. Med.* 231: 1346-1352, 2006) to generated pAT385 (FIG. 8B). rbcLT, tobacco gene encoding chloroplast RuBisCO large subunit; psbARPro, rice promoter of the herbicide binding D1 protein of the photosystem (PSII) reaction center; psbARTer, tobacco terminator of the herbicide binding D1 protein of the photosystem (PSII) reaction center; rrnRPro, rice promoter of rRNA operon; aadA, aminoglycoside 3'-adenylyltransferase; rbcLRTer, rice terminator of chloroplast RuBisCO large subunit in rice; accDT, tobacco gene encoding chloroplast acetyl-CoA carboxylase-subunit.

FIGS. 9A-9D show plastid transformation and identification of tobacco transformed with plasmid pAT385. (A) Shoot regeneration following tobacco plastid transformation on shoot-inducing medium (RMOP medium) containing 500 mg/l spectinomycin dihydrochloride, one month after bombardment. (B) Transplastomic tobacco with roots after 1 month of culture on MS medium containing 500 mg/l spectinomycin. (C) Schematic map showing integration of pAT385-derived DNA in the tobacco chloroplast genome by homologous recombination. ML347 (SEQ ID NO:18), ML916 (SEQ ID NO:16) and ML917 (SEQ ID NO:17) are primers used in PCR amplification for detection of recombinant DNA inserts following plastid transformation. (D) PCR analyses on pAT385 transplastomic line. Total DNA samples extracted from wild type (FIG. 9D, lane 1), pMLV-HisA line (FIG. 9D, lane 2) and the pAT385 transplastomic line (FIG. 9D, lane 3) were amplified using primers pairs ML347/ML917 and ML916/ML917. The expected 1.3-kb and 1.1-kb bands were obtained from the pAT385 transplastomic line.

BRIEF DESCRIPTION OF THE SEQUENCES

SEQ ID NO: 1
(5'-ATATGGATCCCACGCGTTGTCCTCGTCTTCT-3')
is a forward primer for ACBP6 designated "ML750"

SEQ ID NO: 2
(5'-AATATATCATCTTGAATTCAACTG-3')
is a reverse primer for ACBP6 designated "ML751".

SEQ ID NO: 3
(5'-CGGGATCCGAAAATGTCAATCTTTGGTTTGATCTTCGC-3')
is a forward primer for ACBP1 designated "ML179".

SEQ ID NO: 4
(5'-GTCTACAATTGGAATCCTTCTTCTC-3')
is a reverse primer for ACBP1 designated "ML759".

-continued

SEQ ID NO: 5
(5'-TCAAGGGGAGAGTTTCC-3')
is a forward primer for ACBP2 designated "ML194".

SEQ ID NO: 6
(5'-CGTCACCCAGAGGAGTC-3')
is a reverse primer for ACBP2 designated "ML205".

SEQ ID NO: 7
(5'-CTCTCGAGATGGTGGAGAACGATTTGAGT-3')
is a forward primer for ACBP3 designated "ML783".

SEQ ID NO: 8
(5'-ACGAGCTCACATCATACTCTTAGGGAATACCA-3')
is a reverse primer for ACBP3 designated "ML784".

SEQ ID NO: 9
(5'-AGCTCGAGATGGCTATGCCTAGGGCAAC-3')
is a forward primer for ACBP4 designated "ML849".

SEQ ID NO: 10
(5'-CGGAGCTCAATGGCATTACCGGACCAAA-3')
is a reverse primer for ACBP4 designated "ML850".

SEQ ID NO: 11
(5'-CGGATCCAATGGCTCACATGGTGAGAGCAG-3')
is a forward primer for ACBP5 designated "ML352".

SEQ ID NO: 12
(5'-CGAATTCTCATGGGCACTCATGTTTTAGGC-3')
is a reverse primer for ACBP5 designated "ML353".

SEQ ID NO: 13
(5'-GCTCGAAGACGATCAGATACC-3')
is a forward primer for 18S designated "18S-F".

SEQ ID NO: 14
(5'-AGAAAGAGCTCTCAGCTCGTC-3')
is a reverse primer for 18S designated "18S-R".

SEQ ID NO: 15
(5'-CAATCCCACTATCCTTCGCAAGACC-3')
is a 35S promoter-specific forward primer designated
"35SB".

SEQ ID NO: 16
(5'-TGGGGCCCATGGCTGATTGGTATCAGC-3')
is an ACBP1 cDNA fragment primer designated "ML916".

SEQ ID NO: 17
(5'-GCATCGATCTTTGACACACAATTTTAAAG-3')
is an ACBP1 cDNA fragment primer designated "ML917".

SEQ ID NO: 18
(5'-CACACAAATCGGTAGAGCTTAT-3')
is the sequence of primer "ML347".

SEQ ID NO: 19
(Met Arg Gly Ser His His His His His His Gly Met

Ala Ser Met Thr Gly Gly Gln Gln Met Gly Arg Asp

Leu Tyr Asp Asp Asp Asp Lys Asp Arg Trp Ile Arg

Pro Arg Asp Leu Gln Leu Val Pro Trp Asn Ser Arg)
is the N-terminus peptide sequen-
ce of the recombinant
(His)6-ACBP2 fusion protein encoded by pRSET C.

SEQ ID NO: 20
(5'-CGGGATCCGAAAATGTCGCTAATCTCTATCCTCCTCG-3')
is an ACBP1 specific primer designated "ML190".

SEQ ID NO: 21
(5'-ATGGGTGATTGGGCTCAACT-3')
is an ACBP2 specific primer designated "ML902".

-continued

SEQ ID NO: 22
(5'-TTAGTCTGCCTGCTTTGCAG-3')
is an ACBP2 specific primer designated "ML903".

SEQ ID NO: 23
(5'-TTCTCCGTCTTACACCGATT-3')
is an ACBP6 specific primer designated "ML812".

SEQ ID NO: 24
(5'-CTTGATGAGGCATTTAGTGC-3')
is a forward primer specific to the acyl-CoA-
binding-domain of ACBP1.

SEQ ID NO: 25
(5'-TGGGTAAAGCTGAGTAACAAG-3)
is a reverse primer specific to the acyl-CoA-
binding-domain of ACBP1.

SEQ ID NO: 26
is an amino acid sequence of Arabidopsis ACBP6
protein.

SEQ ID NO: 27
is an amino acid sequence of Arabidopsis ACBP1
protein.

SEQ ID NO: 28
is an amino acid sequence of Arabidopsis ACBP2
protein.

SEQ ID NO: 29
is an amino acid sequence of Arabidopsis ACBP3
protein.

SEQ ID NO: 30
is an amino acid sequence of Arabidopsis ACBP4
protein.

SEQ ID NO: 31
is an amino acid sequence of Arabidopsis ACBP5
protein.

DETAILED DESCRIPTION OF THE INVENTION

As used herein, the term "modified plant or plant parts" refers to a plant or plant part, whether it is attached or detached from the whole plant. It also includes progeny of the modified plant or plant parts that are produced through sexual or asexual reproduction.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding an ACBP operably linked to a transcriptional control element (for example, a promoter) to which an endogenous (naturally-occurring) ACBP coding sequence is not normally operably linked. Another example of a heterologous nucleic acid is a high copy number plasmid comprising a nucleotide sequence encoding an ACBP. Another example of a heterologous nucleic acid is a nucleic acid encoding an ACBP, where a host cell that does not normally produce ACBPs is genetically modified with the nucleic acid encoding ACBP; because ACBP-encoding nucleic acids are not naturally found in the host cell, the nucleic acid is heterologous to the genetically modified host cell.

"Recomnbinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, for example, the term "recombinant" polynucleotide or nucleic acid refers to one which is not naturally occurring, for example, is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding ACBPs in Example 3 represent exogenous nucleic acids to *E. coli*. These nucleic acids were cloned from *Arabidopsis*. In *Arabidopsis*, the gene sequences in their native location on the chromosome encoding those ACBPs would be "endogenous" nucleic acids.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The terms "transformation" or "transformed" are used interchangeably herein with "genetic modification" or "genetically modified" and refer to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (for example, a cell line) cultured as a unicellular entity, which eukaryotic or prokaryotic cells can be, or have been, used as recipients for a nucleic acid (for example, an expression vector that comprises a nucleotide sequence encoding one or more gene products such as ACBPs), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (for example, a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, for example, an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation or transcriptional control region(s) (for example, a promoter), the coding region for the protein of interest, and a transcriptional termination region. Transcriptional control regions include those that provide for overexpression of the protein of interest in the genetically modified host cell; those that provide for inducible expression, such that when an inducing agent is added to the culture medium, transcription of the coding region of the protein of interest is induced or increased to a higher level than prior to induction.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available. Fragments of full-length proteins can be produced by techniques well known in the art, such as by creating synthetic nucleic acids encoding the desired portions; or by use of Bal 31 exonuclease to generate fragments of a longer nucleic acid.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at nebi.nlm.nih.gov/BLAST. See, e.g., Altschul et al. (1990), *J. Mol. Biol.* 215:403-410. Another alignment algorithm is FASTA, available in the Genetics Computing Group (GCG) package, from Madison, Wis., USA, a wholly owned subsidiary of Oxford Molecular Group, Inc. Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the term "variant" refers either to a naturally occurring genetic mutant of ACBP or a recombinantly prepared variation of ACBP, each of which contain one or more mutations in its DNA. The term "variant" may also refer to either a naturally occurring variation of a given peptide or a recombinantly prepared variation of a given peptide or protein in which one or more amino acid residues have been modified by amino acid substitution, addition, or deletion. Preferably, the variants include less than 25, less than 20, less than 15, less than 10, less than 5, less than 4, less than 3, or less than 2 amino acid substitutions, rearrangements, insertions, and/or deletions relative to *Arabidopsis* ACBPs. In this regard, the term "variant" can encompass fragments, derivatives, and analogs of *Arabidopsis* ACBPs.

To generate a subject genetically modified host cell, one or more nucleic acids comprising nucleotide sequences encoding one or more ACBP polypeptides that relieve lead accumulation-induced growth inhibition is introduced stably or transiently into a parent host cell, using established techniques, including, but not limited to, electroporation, calcium phosphate precipitation, DEAE-dextran mediated transfection, liposome-mediated transfection, particle bombardment, and the like. For stable transformation, a nucleic acid will generally further include a selectable marker, for example, any of several well-known selectable markers such as neomycin resistance, ampicillin resistance, tetracycline resistance, chloramphenicol resistance, kanamycin resistance, and the like.

Where a parent host cell has been genetically modified to produce two or more ACBPs, nucleotide sequences encoding the two or more ACBPs will in some embodiments each be contained on separate expression vectors. Where the host cell is genetically modified to express one or more ACBPs, nucleotide sequences encoding the one or more ACBPs will in some embodiments be contained in a single expression vector. Where nucleotide sequences encoding the one or more ACBPs are contained in a single expression vector, in some embodiments, the nucleotide sequences will be operably linked to a common control element (for example, a promoter), such that the common control element controls expression of all of the ACBP-encoding nucleotide sequences on the single expression vector.

Where nucleotide sequences encoding the ACBP(s) are contained in a single expression vector, in some embodiments, the nucleotide sequences will be operably linked to different control elements (for example, a promoter), such that, the different control elements control expression of each of the ACBP-encoding nucleotide sequences separately on a single expression vector.

A subject screening method can involve introducing an exogenous nucleic acid into a host cell, producing a test cell, where the host cell is one that exhibits growth inhibition when lead (or another metal present as a divalent cation, such as copper or cadmium, etc.) is present in the growth medium in a growth-inhibiting amount. When an exogenous nucleic acid comprising a nucleotide sequence that encodes an ACBP is introduced into the host cell, growth inhibition of the test cell is relieved. Thus, a reduction in growth inhibition indicates that the exogenous nucleic acid encodes ACBP, where the encoded ACBP is produced at a level and/or has an activity that relieves the lead accumulation-induced growth inhibition. A reduction in growth inhibition includes an at least about 10%, at least about 20%, at least about 30%, at least about 40%, at least about 50%, at least about 60%, at least about 70%, at least about 80%, at least about 90%, or more, reduction in growth inhibition. In some embodiments, the ACBP encoded by the exogenous nucleic acid reduces the growth inhibition such that the rate of cell growth is restored to the rate of cell growth of the host cell when grown under conditions where lead is not present in growth inhibiting amounts.

In some embodiments, for example, where the exogenous nucleic acid is a plurality of exogenous nucleic acids (such as, for example, a cDNA library, a genomic library, or a population of nucleic acids, each encoding an ACBP with a different amino acid sequence, etc.), the exogenous nucleic acids are introduced into a plurality of host cells, forming a plurality of test cells. The test cells are in some embodiments grown in culture under conditions such that lead is present in a growth inhibiting and/or death-inducing amount; those test cells comprising an exogenous nucleic acid that comprises nucleotide sequences encoding an ACBP will grow faster than test cells that do not comprise an exogenous nucleic acid that comprises nucleotide sequences encoding an ACBP, or those test cells comprising an exogenous nucleic acid that comprises nucleotide sequences encoding an ACBP will live, while test cells that do not comprise an exogenous nucleic acid that comprises nucleotide sequences encoding ACBP will die or otherwise be adversely affected.

In some embodiments, the method further involves isolating an exogenous nucleic acid from a test cell, where the exogenous nucleic acid is one that that relieves growth inhibition in a subject screening method. Methods of isolating the exogenous nucleic acid from a test cell are well known in the art. Suitable methods include, but are not limited to, any of a number of alkaline lysis methods that are standard in the art.

In some embodiments, a subject screening method will further comprise further characterizing a candidate gene product. In these embodiments, the exogenous nucleic acid comprising nucleotide sequence(s) encoding an ACBP(s) are isolated from a test cell; the gene product(s) are expressed in a cell and/or in an in vitro cell-free transcription/translation system. In some embodiments, the exogenous nucleic acid is subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists. In addition, the gene product(s) are expressed in a cell and/or in an in vitro cell-free transcription/translation system; and the effect of the gene product(s) on a metabolic pathway intermediate or other metabolite is analyzed.

Exogenous nucleic acids that are suitable for introducing into a host cell, to produce a test cell, include, but are not limited to, naturally-occurring nucleic acids isolated from a cell; naturally-occurring nucleic acids that have been modified (for example, by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like.

Exogenous nucleic acids that are suitable for introducing into a host cell include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis. In some embodiments, exogenous nucleic acids are a cDNA library made from cells, either prokaryotic cells or eukaryotic cells. In some embodiments, exogenous nucleic acids are a genomic DNA library made from cells, either prokaryotic cells or eukaryotic cells.

Nucleic acids will in some embodiments be mutated before being introduced into a host cell. Methods of mutating a nucleic acid are well known in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, .gammna.-iiradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable method for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 16, PMS 12, MLH 1, GTBP, ERCC-1, and the like). Methods of mutating nucleic acids are well known in the art, and any known method is suitable for use. See, e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

In many embodiments, the exogenous nucleic acid is inserted into an expression vector. Expression vectors that are suitable for use in prokaryotic and eukaryotic host cells are known in the art, and any suitable expression vector can be used. Suitable expression vectors are as described above.

As noted above, an exogenous nucleic acid will in some embodiments be isolated from a cell or an organism in its natural environment. In some embodiments, the nucleic acid of the cell or organism will be mutated before nucleic acid is isolated from the cell or organism. In other embodiments, the exogenous nucleic acid is synthesized in a cell-free system in vitro.

In some embodiments, the exogenous nucleic acid is a synthetic nucleic acid. In some embodiments, a synthetic nucleic acid comprises a nucleotide sequence encoding a variant ACBP, for example, an ACBP that differs in amino acid sequence by one or more amino acids from a naturally-occurring ACBP or other parent ACBP. In some embodiments, a variant ACBP differs in amino acid sequence by one amino acid, two amino acids, three amino acids, four amino acids, five amino acids, six amino acids, seven amino acids, eight amino acids, nine amino acids, or amino acids, or more, compared to the amino acid sequence of a naturally-occurring parent ACBP. In some embodiments, a variant ACBP differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, compared to the amino acid sequence of a naturally-occurring parent ACBP.

In some embodiments, a variant ACBP is encoded by a nucleic acid that hybridizes under stringent hybridization conditions to a nucleic acid encoding a known ACBP. In other embodiments, a variant ACBP is encoded by a nucleic acid that hybridizes under moderate hybridization conditions to a nucleic acid encoding a known ACBP.

In some embodiments, a nucleic acid comprising a nucleotide sequence encoding a naturally-occurring ACBP is mutated, using any of a variety of well-established methods, giving rise to a nucleic acid comprising a nucleotide sequence encoding a variant ACBP. Suitable mutagenesis methods include, but are not limited to, chemical mutation methods, radiation-induced mutagenesis, and methods of mutating a nucleic acid during synthesis, as described supra. Thus, for example, a nucleic acid comprising a nucleotide sequence encoding a naturally-occurring ACBP is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant ACBP. See, e.g., Greener et al., "An Efficient Random Mutagenesis Technique Using an *E. coli* Mutator Strain", *Methods in Molecular Biology*, 57:375-385 (1995). Saturation mutagenesis techniques employing a polymerase chain reaction (PCR) are also well known and can be used. See, e.g., U.S. Pat. No. 6,171,820. Nucleic acids comprising a nucleotide sequence encoding a variant ACBP are identified by the ability to relieve growth inhibition caused by lead.

Nucleotide sequences encoding ACBPs are known in the art, and any known ACBP-encoding nucleotide sequence can be altered to generate a synthetic nucleic acid for use in a subject method.

An embodiment of the invention provides a host cell comprising a vector according to the invention. Other embodiments include plant plastid transformation vectors or nuclear transformation vectors containing nucleotide sequences encoding *Arabidopsis* ACBPs, such as containing the full-length ACBPs, or variants or fragments thereof, for the expression of ACBPs or ACBP polypeptides or variants exhibiting similar lead-binding activities to full-length ACBPs. These plant vectors may contain other sequences for the generation of chimeric ACBP polypeptides which may contain mutations, deletions, or insertions of the ACBP polypeptides.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a genetically modified host cell" includes a plurality of such host cells and reference to "the ACBP" includes reference to one or more *Arabidopsis* ACBPs and equivalents thereof that will become known to those skilled in the art in view of this disclosure, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Plant Materials, Growth Conditions and Treatment

*Arabidopsis thaliana* wild-type Columbia (ecotype Col-0), ACBP1- and ACBP3-overexpressing transgenic plants (ecotype Col-0) were grown under 8 h dark at 21° C. and 16 h light at 23° C. cycles. For Pb(II)-inducible gene expression analysis, *Arabidopsis* seedlings were grown for 3 weeks in continuous light, treated with 1 mM Pb(NO$_3$)$_2$ or water (as control), and shoot and root samples were collected at 24 h post-treatment. For Pb(II) sensitivity tests, *Arabidopsis* seedlings were surface-sterilized and grown on Murashige and Skoog (*Physiol. Plant.* 15: 473-497, 1962) medium containing 2% sucrose with or without 0.75 mM Pb(NO$_3$)$_2$ (Sigma-Aldrich, St. Louis) for 2 to 3 weeks.

Example 2

ACBP Transcripts are Induced by Pb(II) Treatment

To determine if the regulation of *Arabidopsis* ACBP mRNAs responds to Pb(II) stress, we performed reverse transcription-PCR(RT-PCR) using root tissue RNA following treatment with 1 mM Pb(NO$_3$)$_2$. For RT-PCR, total RNA was extracted with TRIzol (Invitrogen) reagent, according to the manufacturer's protocol, from roots of 3-week-old wild-type *Arabidopsis* (Col-0) seedlings in the presence or absence (water as control) of 1 mM Pb(NO$_3$)$_2$. RT-PCR analysis was performed as according to the manufacturer (Invitrogen Cat No. 12371-019). Specific primers were designed based on mRNA sequences. Primers used for RT-PCR analysis of ACBP6 were ML750 (SEQ TD NO:1) and ML751 (SEQ ID NO:2); ACBP1, ML179 (SEQ ID NO:3) and ML759 (SEQ ID NO:4); ACBP2, ML194 (SEQ ID NO:5) and ML205 (SEQ ID NO:6); ACBP3, ML783 (SEQ ID NO:7) and ML784 (SEQ ID NO:8); ACBP4, ML849 (SEQ ID NO:9) and ML850 (SEQ ID NO:10); ACBP5, ML352 (SEQ ID NO:11) and ML353 (SEQ ID NO:12); 18S, 18S-F (SEQ ID NO:13) and 18S-R (SEQ ID NO:14).

The mRNA expressions of ACBP1 to ACBP5 was observed to increase in roots 24 h after Pb(II) treatment on RT-PCR analysis (FIG. 1). Surprisingly, the transcript of ACBP6 which encodes the homolog of human 9-kDa ACBP implicated as a molecular target for Pb(II) in vivo (Smith et al., *Chemico-Biological Interactions* 115: 39-52, 1998), showed little change upon Pb(II) treatment (FIG. 1). These results indicate that *Arabidopsis* ACBP1 to ACBP5, to a greater extent than ACBP6, play a role in Pb(II) stress.

Example 3

Expression of Recombinant ACBPs in *E. coli* BL21DE3 Cells

Each of the six cDNAs encoding *Arabidopsis* ACBPs were cloned in plasmid pRSET (Invitrogen) for expression in *Escherichia coli* according to protocols specified by Invitrogen, as $(His)_6$-tagged ACBP recombinant proteins that were subsequently used to ascertain if these $(His)_6$-ACBPs bind Pb(II) in vitro. The ACBP-pRSET derivatives were expressed in bacterial (*Escherichia coli* BL21DE3) cells and subsequently harvested for purification of the $(His)_6$-tagged proteins following methods described in Leung et al. (*Planta* 223: 871-881, 2006). These purified ACBP recombinant proteins were then tested for the ability to bind lead using Pb(II)-binding assays (Funaba and Mathews, *Mol. Endocrinol.* 14: 1583-1591, 2000).

*E. coli* BL21(DE3)Star pLysS (Invitrogen, Carlsbad, Calif., USA) were transformed with each of the six plasmids expressing recombinant ACBP6 (10-kDa ACBP) and ACBP1 to ACBP5. Transformed cells were grown to $OD_{600nm}$=0.4, as measured using a UV-spectrophotometer (Shimadzu Model UV-1206, Japan), and induced with 1 mM IPTG. Each $(His)_6$-ACBP was harvested 3 h after IPTG-induction for extraction of soluble and insoluble proteins following procedures described by Invitrogen (Carlsbad, Calif., USA). The detailed procedure for the purification of each recombinant ACBP has been previously described for ACBP1 (Chye, *Plant Mol. Biol.* 38: 827-838, 1998), ACBP2 (Chye et al., *Plant Mol. Biol.* 44: 711-721, 2000), ACBP3 (Leung et al., *Planta* 223: 871-881, 2006) and ACBP4 and ACBP5 (Leung et al., *Plant Mol. Biol.* 55: 297-309, 2004) and is briefly described below in Example 4. Harvested protein samples were analyzed on sodium dodecyl sulfate-polyacrylamide gel electrophoresis (SDS-PAGE) according to Laemmli (*Nature* 227:680-685, 1970).

Recombinant $(His)_6$-ACBP1 fusion protein was expressed from plasmid pAT61 in *E. coli* as described (Chye, *Plant Mol. Biol.* 38: 827-838, 1998). Plasmid pAT61 was produced by cloning an ExoIII deletion derivative of the ACBP1 cDNA on a 1.1 kb EcoRI fragment in-frame to the EcoRI site of pRSET B vector (Chye, *Plant Mol. Biol.* 38: 827-838, 1998). The recombinant $(His)_6$-ACBP1 fusion protein lacks the first 40 amino acids at the N-terminal of ACBP1 (Chye, *Plant Mol. Biol.* 38: 827-838, 1998).

The expression of recombinant $(His)_6$-ACBP1 fusion protein as described Chye, *Plant Mol. Biol.* 38: 827-838, 1998 is illustrated in detail as follows. "Recombinant ACBP 1 protein expression in *E. coli* was achieved with the pRSET protein expression vectors (Invitrogen Xpress System). The 1.4 kb EcoRI fragment containing the ACBP 1 cDNA could not be directly cloned in the pRSET vector for protein expression because an in-frame 'TGA' stop codon is located in the 5'-untranslated region of the ACBP1 cDNA 40 to 42 nucleotides u stream from the 'ATG' start codon. Hence to remove the in-frame 'TGA' plasmid pAI25, a pBluescript SK-derivative containing the ACBP1 cDNA, was subjected to ExoIII (Stratagene) deletion from the 5' end of the ACBP 1 cDNA. The 1.4 kb ACBP 1 cDNA in plasmid pAT25 is inserted into the EcoRI site in an orientation such that the 5' end of the cDNA is adjacent to the SalI site of the vector. Plasmid pAT25 was linearized with SalI and KpnI before ExoIII treatment using the ExoIII-Mung Bean Deletion Kit (Stratagene) following the instructions of the manufacturer. Subsequently EcoRI-SmaI adaptors were ligated to the DNA which was then recircularized for bacterial tranformation. ExoIII-deleted derivatives were analysed by nucleotide sequence analysis to determine the end-point of each deletion.

The EcoRI fragment from each of two independently ExoIII-derived plasmids was cloned in the EcoRI site of pRSET C and pRSET B to yield plasmids, pAT 59 and pAT 61, respectively. The ACBP1 cDNA in plasmid pAT 59 encodes part of the transmembrane domain in ACBP1 while plasmid pAT 61 completely lacks the transmembrane-encoding, region. The EcoRI site in the pRSET vector lies downstream from the T7 promoter, which drives expression of the recombinant $(His)_6$-ACBP fusion protein. *E. coli* BL21(DE3) [40] cells transformed with each recombinant ACBP 1 plasmid were cultured; fusion protein expression was induced with 1 mM isopropylthio-β-D-galactoside (IPTG) and soluble protein and insoluble protein were extracted according to the procedures described by Invitrogen."

Recombinant $(His)_6$-ACBP2 fusion protein expression in *E. coli* was achieved by cloning a 1.3-kb ACBP2 cDNA on an EcoRI fragment, in-frame to the EcoRI site of vector pRSET C (Invitrogen Xpress System) to yield plasmid pACBP2. This 1.3 kb cDNA is incomplete at the 5'-end, lacking the 0.19 kb 5'-untranslated region and the methionine start codon. To confirm that the 1.3 kb cDNA was cloned in-frame to the $(His)_6$ tag, the DNA sequence of pACBP2 across the EcoRI site was subsequently verified. The EcoRI site in the pRSET C vector lies downstream from the T7 promoter, which drives expression of the recombinant $(His)_6$-ACBP2 fusion protein. At the N-terminus of this recombinant protein, the peptide sequence encoded by pRSET C (MRGSHHHHHG-MASMTGGQQMGRDLYDDDDIDRWIR-PRDLQLVPWNSR), designated SEQ ID NO:19, is fused to amino acid residue Gly-2 on the ACBP2 peptide. The expected molecular mass of this recombinant protein was predicted using the GCG analysis package (Genetics Computer Group). *E. Coli* cells transformed with pACBP2 were cultured and $(His)_6$-ACBP2 fusion protein expression was induced with 1 mM IPTG; soluble protein and insoluble protein were extracted according to the procedures described by Invitrogen. Protein concentrations of these protein extracts were determined by the method of Bradford (*Anal. Biochem.* 72: 248-254, 1976). The optimal time for protein induction was determined at 4 h after IPTG induction, according to the procedure described by Invitrogen. Protein samples (10 μg) of soluble protein extract and of insoluble protein extract, taken at various time intervals after addition of 1 mM IPTG, were analyzed by SDS-PAGE according to Laemmli (*Nature* 227:680-685, 1970).

Recombinant $(His)_6$-ACBP3, cloned in pRSET B (Invitrogen)-derived vector pAT223, was prepared from *E. coli* BL21 (DE3)Star pLys (Invitrogen) transformants as described in Leung et al. (*Planta* 223: 871-881, 2006). Transformed cells were grown to $OD_{600\ nm}$=0.4, as measured using a UV-spectrophotometer (Shimadzu Model UV-1206, Japan), and induced with 1 mM IPTG. (His)$_6$-ACBP3 was harvested 3 h after IPTG-induction for extraction of soluble and insoluble proteins following procedures described by Invitrogen (Carlsbad, Calif., USA).

Recombinant (His)$_6$-ACBP4 and (His)$_6$-ACBP5, expressed from pRSET B (Invitrogen)-derived vectors pAT184 and pAT185, respectively, were prepared from *E. coli* BL21(DE3)Star pLys (Invitrogen) transformants as described in Leung et al. (*Plant Mol. Biol.* 55: 297-309, 2004).

The preparation of recombinant (His)$_6$-ACBP4 and (His)$_6$-ACBP5 as described in Leung et al. Plant Mol. Biol. 55: 297-309, 2004 is illustrated in detail as follows. "*Escherichia coli* BL21(DE3)Star pLysS (Invitrogen) was transformed with each of plasmids pAT184 and pAT185. Transformed cells were grown to OD$_{600}$=0.4 (Shimadzu UV-spectrophotometer Model UV-1206) and induced with 1 mM IPTG. Since (His)$_6$-ACBP4 and (His)$_6$-ACBP5 were expressed even in the absence of induction, IPTG was omitted in the subsequent expression of these two proteins. The cells were incubated for a further 3 h at 37° C. with vigorous shaking in the absence of IPTG after OD$_{600}$=0.4 was attained and soluble and insoluble proteins were extracted according to procedures of Invitrogen."

Recombinant (His)$_6$-ACBP6 (size of recombinant protein inclusive of His-tag is 18.9 kDa) cloned in pRSET B (Invitrogen)-derived vector pAT335, was prepared from *E. coli* BL21(DE3)Star pLys (Invitrogen) transformants. A 0.65-kb PCR fragment consisting of the full-length cDNA encoding *Arabidopsis* ACBP6 was generated by RT-PCR using primers ML750 (5'-ATATGGATCCCACGCGTTGTCCTCGTCT-TCT-3'), designated SEQ ID NO:1, and ML751 (5'-AATATATCATCTTGAATTCAACTG-3'), designated SEQ ID NO:2. The 0.65-1 kb fragment was cloned into pGEM-T EASY vector (Promega). After confirmation of the insert by DNA sequencing analysis, the SacI-EcoRI fragment corresponding to the coding region was cloned in-frame to vector pRSET B (Invitrogen) to yield plasmid pAT335. The molecular mass of this (His)$_6$-tagged ACBP expressed from this plasmid was predicted using the GCG (Genetics Computer Group, Wisconsin Software Version 10.2) programme to be 18.9-kDa. The plasmid pAT335 was introduced into *E. coli* BL21 (DE3)Star pLysS (Invitrogen, Carlsbad, Calif., USA) and then cultured to OD$_{600nm}$=0.4, as measured using a UV-spectrophotometer (Shimadzu Model UV-1206, Japan), and subsequently induced with 1 mM IPTG. After IPTG-induction for 3 h, the (His)$_6$-tagged ACBP expressing cells were harvested for extraction of insoluble protein following procedures described by Invitrogen (Carlsbad, Calif., USA). Protein concentration of bacterial crude extracts was determined following the method of Bradford (*Anal Biochem* 72: 248-254, 1976). Subsequently, 10 µg of the each protein sample were separated by 15% polyacrylamide gel and then electrophoretically transferred to ECL membrane (Amersham, Buckinghamshire, UK) using the Trans-Blot cell (Bio-Rad) or stained by Coomassie Brilliant Blue.

Protein concentrations of bacterial crude extracts were determined by the method of Bradford (*Anal. Biochem.* 72: 248-254, 1976) and samples (10 µg) harvested at various time intervals were analyzed by SDS-PAGE according to Laemmli (*Nature* 227: 680-685, 1970). Subsequently the 10% polyacrylamide gel was stained with Coomassie Blue or used for western blotting (Sambrook et al. In: *Molecular Cloning: A Laboratory Manual*, Second Edition. Cold Spring Harbor Laboratory Press, Cold Spring Harbor, pp 18.60-18.73, 1989) by electrophoretically transfer of proteins to ECL membranes (Amersham, Buckinghamshire, UK) from the polyacrylamide gel using the Trans-Blot® cell (Bio-Rad) following the manufacturer's instructions. The QIAexpress Ni-NTA Conjugate (Qiagen, Valencia, Calif., USA) was used according to the manufacturer to detect the expression of the (His)$_6$-tagged ACBP proteins.

Example 4

Purification of Recombinant (His)$_6$-Tagged ACBPs from *E. coli* Transformants

Recombinant (His)$_6$-tagged ACBPs were purified through affinity columns of Ni-NTA Agarose (Qiagen, Valebcia, Calif., USA) following instructions of the manufacturer as previously described (Leung et al., *Plant Mol. Biol.* 55: 297-309, 2004; Leung et al., *Planta* 223: 871-881, 2006).

(His)$_6$-ACBP1 expressed in the soluble fraction of *E. Coli* extracts and was purified through an affinity column of Ni-NTA Agarose (Qiagen, Valencia, Calif., USA) according to the instructions of the supplier.

Batch extractions of (His)$_6$-ACBP6, (His)$_6$-ACBP2, (His)$_6$-ACBP3, (His)$_6$-ACBP4 and (His)$_6$-ACBP5 were carried out under denaturing conditions. The (His)$_6$-ACBP2 fusion protein eluted in Buffer E (8 M urea, 0.1 M NaH$_2$PO$_4$, 0.01 M Tris pH 4.5, 5% glycerol). The (His)$_6$-ACBP3, (His)$_6$-ACBP4 and (His)$_6$-ACBP5 fusion proteins eluted in both buffer D (8 M urea, 0.1 M NaH$_2$PO$_4$, 0.01 M Tris-Cl, pH 5.9, 5% glycerol) and buffer E (8 M urea, 0.1 M NaH$_2$PO$_4$, 0.01 M Tris-Cl, pH 4.5, 5% glycerol). After dialysis and refolding in 50 mM HEPES sodium salt, 200 mM NaCl, 2 mM MgCl$_2$, 5 mM EDTA, 10% glycerol, 0.005% (v/v) Tween-20, pH 7.9 at 4° C., each recombinant protein was purified through an affinity column of Ni-NTA Agarose (Qiagen, Valencia, Calif., USA) according to the instructions of the supplier.

Each purified (His)$_6$-tagged recombinant fusion protein was concentrated using Centricon-10 (Amicon) spin columns and was subsequently used for in vitro binding assays. The concentrations of purified (His)$_6$-ACBPs were determined by weighing freeze-dried recombinant protein and measurements of absorbance at 280 nm (Layne, *Meth. Enzymol.* 3: 447-454, 1957).

Example 5

Lead-Binding Assays

Lead-binding assays and fluorescence measurements were carried out according to Funaba and Mathews (*Mol. Endocrinol.* 14:1583-1591, 2000) with minor modifications. Briefly, 3.2 µM of each purified (His)$_6$-ACBP protein which was equilibrated in 20 mM phosphate buffer (pH 7.2) with 200 mM NaCl, were labeled with 8 µl of 200 mM dansyl aziridine (Molecular Probes, Cat. No. D151) and reacted for 2 h in a 1.5 ml Eppendorf tube at room temperature. The dansylated (His)$_6$-ACBP proteins were then distributed to 8 wells of a 96-well microtiter plate (Nunc Cat. No. 236105). Various concentrations (0, 1.0, 2.0, 3.0, 4.0, 5.0, 7.0 and 9.0 µM) of Pb(NO$_3$)$_2$ (Aldrich, Cat. No. 203580) solutions were added and the reactions were incubated at room temperature for 1 h.

Fluorescence measurements were performed using a BIO-TEK FL600 Fluorescence Plate Reader (BIO-TEK Instrument, INC, USA) with excitation wavelength set at 360/40 nm and emission wavelength set at 530/25 nm. Prior to binding with lead, the dansyl aziridine coupled (His)$_6$-ACBP recombinant proteins are sensitive to the conformational changes. After binding to Pb(II) molecules, the dansylated (His)$_6$-ACBP recombinant proteins would change their conformations and the dye will show an increase in fluorescence excitation. Hence, a difference in fluorescence in the presence and absence of Pb(II) molecules would indicate binding of a (His)$_6$-ACBP recombinant protein with Pb(II). Each experiment was repeated three times to ascertain results.

Figure 2A:
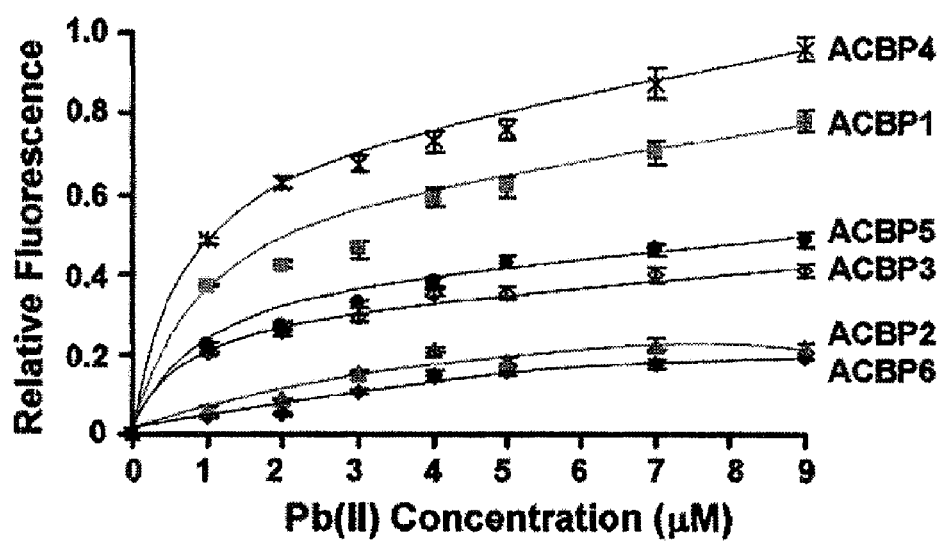

Our results indicate that recombinant ACBPs bind Pb(II) in vitro. The relative fluorescence intensities of (His)$_6$-ACBPs increased in the presence of Pb(II) in a dose-dependent manner from 1 to 9 µM of Pb(II), indicative of binding to Pb(II) (FIG. 2A). The relative fluorescence intensity of (His)$_6$-ACBP4 and (His)$_6$-ACBP1 were observed to be much higher than the other recombinant ACBPs.

Example 6

Heavy-Metal-Binding Assays Using Metal-Chelate Affinity Chromatography

The coding regions of ACBP1, ACBP2 and ACBP6 were generated by RT-PCR for construction of pGEM-T EASY (Promega) derivatives for in vitro transcription/translation. Primers used in RT-PCR were as follows: ACBP1 (ML190 (SEQ ID NO:20) and ML917 (SEQ ID NO:17), ACBP2 (ML902 (SEQ ID NO:21) and ML903 (SEQ ID NO:22)), and ACBP6 (ML812 (SEQ ID NO:23) and ML751 (SEQ ID NO:2)). The PCR products were subsequently cloned into pGEM-T EASY vector (Promega) for in vitro transcription/translation using the TNT® T7/SP6 Coupled Wheat Germ Extract System (Promega) following the manufacturer's instruction. Pb(II)-, Cd(II)-, and Cu(II)-equilibrated matrices for metal-binding assays were prepared by stripping Ni-NTA agarose (Qiagen) of nickel and re-equilibrating with 0.1 M Pb(NO$_3$)$_2$ (Aldrich), CdCl$_2$ (Aldrich), or CuCl$_2$ (Aldrich). Twenty µl of Pb(II)-, Cd(II)-, or Cu(II)-equilibrated matrix, 545 µl of 50 mM KH$_2$PO$_4$, 300 mM NaCl, pH 7.4, and [$^{35}$S]methionine-labeled protein were added to a microfuge tube (Dykema et al., *Plant Mol. Biol.* 41: 139-150, 1999) and rotated on a wheel at 4° C. for 1 h. Subsequently, the matrix was washed 3 times with 1.0 ml of 50 mM KH$_2$PO$_4$, 300 mM NaCl, pH 7.5. The binding protein was eluted with 200 µl of 50 mM KH$_2$PO$_4$, 300 mM NaCl, 500 mM imidazole, pH 4.5, followed by extraction with 200 µl of 2% SDS, 50 mM DTT, heating at 85° C. for 3 min and analysis by SDS-PAGE followed by autoradiography.

Figure 2B:
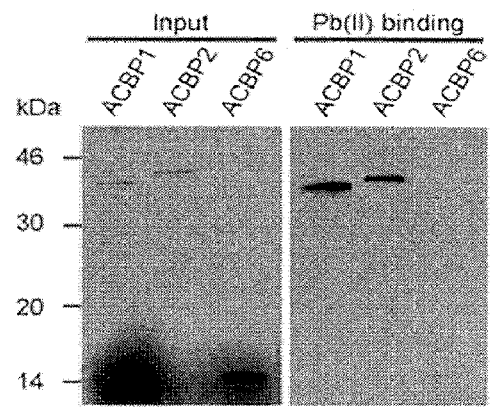
Figure 2C:
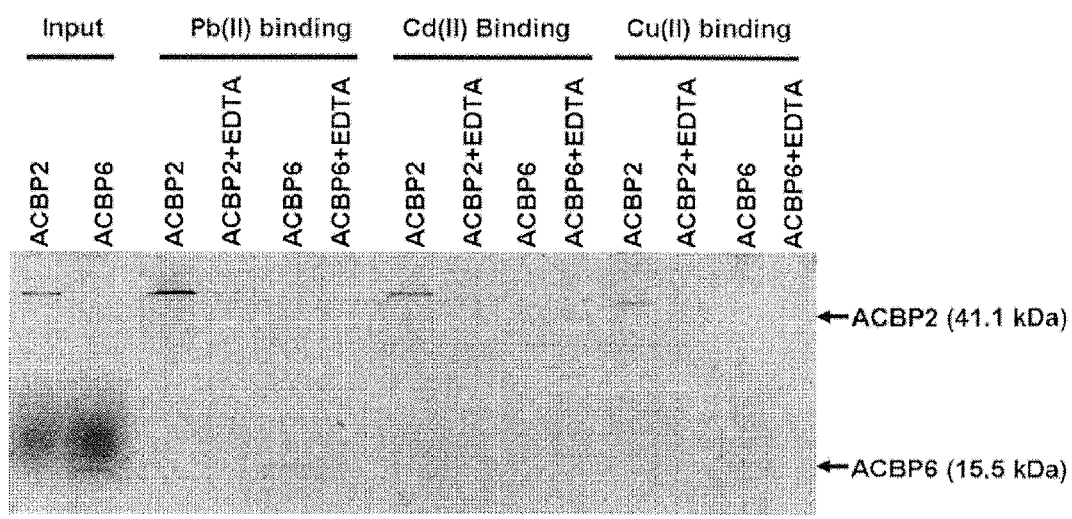

Our results indicate that in vitro translated ACBP1 and ACBP2 bind Pb(II) better than ACBP6 (FIG. 2B). ACBP1 appeared to show slightly better binding than ACBP2 (FIG. 2B). Our results (FIG. 2C) also indicate that in vitro translated ACBP2 also binds Cd(II) and Cu(II) better than ACBP6. Binding of ACBP2 to Pb(II), Cd(II), and Cu(II) was inhibited by the metal chelator, ethylenediaminetetraacetic acid (EDTA), indicating that binding is dependent on divalent cations (FIG. 2C).

Disparity in Pb(II)-binding between in vitro translated ACBP2 (FIG. 2B) and (His)$_6$-ACBP2 (FIG. 2A) may have arisen from differences in protein preparation procedures. (His)$_6$-ACBP2 was prepared from *E. coli* insoluble extracts under denaturing conditions followed by refolding (Chye et al., *Plant Mol. Biol.* 44: 711-721, 2000) in contrast to in vitro translated ACBP2. In comparison, (His)$_6$-ACBP1 was prepared directly from soluble *E. coli* extracts (Chye, *Plant Mol. Biol.* 38: 827-838, 1998). (His)$_6$-ACBP6 (FIG. 2A) and in vitro translated ACBP6 (FIG. 2B) seem to bind Pb(II) less well than ACBP1 despite being a closer homolog to the human ACBP, a molecular target for Pb(II) in vivo (Smith et al., *Chemico-Biological Interactions* 115: 39-52, 1998). Since larger homologs of *Arabidopsis* ACBPs have not been identified in man, the smaller ACBP may be the only available ACBP in humans that binds Pb(II). A comparison of *Arabidopsis* ACBPs at the acyl-CoA-binding domain is shown in FIG. 2D. Ten amino acid residues within the acyl-CoA-binding domain, that are conserved in ACBP1 to ACBP5 but not in ACBP6, are identified (underlined amino acids in "Con" sequence in FIG. 2D). Those 3 conserved amino acid residues that are further conserved in the 9-kDa human ACBP (GenBank Accesssion No. NM_020548) are encircled; these 3 amino acid residues conserved in human ACBP and ACBP1 to ACBP5 may play an important role in binding lead.

Other plant-derived ACBPs can be identified by searching known databases for sequences demonstrating homology to any of the *Arabidopsis* ACBPs 1-6 using techniques well known to those of ordinary skill in the art. Alternatively, to obtain other plant-derived ACBPs, those of ordinary skill in the art can obtain and probe DNA libraries of plant species of interest using routine techniques and probes based on any of *Arabidopsis* ACBPs 1-6 to identify homologous sequences which can then be isolated and expressed. The protein expression products can then be tested to confirm whether they have the ability to bind acyl-CoA esters.

All *Arabidopsis* ACBPs (ACBP1 to ACBP6) show 100% conservation in 13 other amino acid residues (marked with asterisks in "Con" sequence in FIG. 2D). Plant-derived ACBPs and ACBP variants conserved in these residues, at a putative acyl-CoA-binding domain, should retain at least 7 of these 13 conserved residues. While the first 2 conserved residues (marked with asterisks) "F" and "V" may be variably separated (by a spacing of 3 to 6 residues), the last 11 conserved residues are specifically LxxLxxAxxGxxxxxx-PxxxxxxxxxKWxxWxxxxxxxxxEAM, where x denotes any amino acid residue. In ACBP variants or other plant-derived ACBPs, retaining at least 7 of these 13 conserved residues, presence of this domain can be further tested to confirm whether it confers the ability to bind acyl-CoA esters.

FIG. 2D also shows the "Com" (Common) amino acids, displayed below the "Con" (Conserved) amino acids, occurring within the acyl-CoA-binding domain. By definition, "Com" lists the amino acids within the acyl-CoA-binding domains of ACBP1 to ACBP5 that occur at least twice in any of these 5 ACBPs (ACBP1 to ACBP5). FIG. 2D indicates that there is high conservation in amino acids at the acyl-CoA-binding domain of ACBP1 to ACBP5; hence the nucleotide sequence encoding this domain can be PCR-amplified and used as a hybridization probe to identify homologs of *Arabidopsis* ACBP1 to ACBP5 in other organisms.

For example, the nucleotide sequence encoding the acyl-CoA-binding-domain in ACBP1 (amino acids 94 to 180) can be generated using forward primer 5'-CTTGATGAGGCATT-TAGTGC-3' (designated as SEQ ID NO:24) and reverse primer 5'-TGGGTAAAGCTGAGTAACAAG-3' (designated as SEQ ID NO:25) to produce a 0.26-kb DNA fragment that should be able detect other plant-derived nucleotide sequences encoding acyl-CoA-binding domains when it is used as a hybridization probe when screening DNA libraries. For PCR amplification of the acyl-CoA-binding domain in ACBP1, each 25-µl PCR reaction consisted of 25 ng plasmid pAT31 DNA, 10 pmol of each primer of SEQ ID NO:24 and of SEQ ID NO:25, 1 U Taq polymerase (Perkin Elmer), 2.5 µl 10×PCR buffer, 1.5 µl of 25 mM MgCl$_2$ and 0.5 µl each of 10 mM dATP, dGTP, dTTP, and $^{32}$P-labeled dCTP. PCR-amplification was initiated with denaturation at 95° C. for 3 min, followed by 40 cycles of 94° C. for 1 min, 55° C. for 1 min and 68° C. for 4 min and extension at 72° C. for 10 min.

The 0.26-kb PCR-generated radiolabeled probe can be used to screen DNA libraries to identify hybridizing clones that encode ACBP homologs. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). A BLAST search of the NCBI database using, as query sequence, this 0.26-kb nucleotide sequence of ACBP1 that encodes its acyl-CoA-binding domain, yielded 56 "Blast hits" from other species confirming its feasibility as a hybridization probe in screening DNA libraries. These "Blast hits" (with % DNA identity shown in brackets) include GenBank entries, AM476905 (*Vitis vinifera;* 75% identity), AC189237 (*Brassica rapa;* 75%); CT831642 (*Oryza sativa;* 73%); NM_001060827 (*Oryza sativa;* 73%), DQ908250 (*Gossypium hirsutum;* 81%), and EF086012 (*Picea sitchensis;* 69%). We have previously detected in Western blot analysis, using anti-ACBP1 antibodies on total plant protein from *Brassica juncea, Solanum melongena*, lettuce, carrot and potato, the presence of cross-reacting bands similar in molecular mass as *Arabidopsis* ACBP1, suggesting that ACBP1 homologs occur in many diverse plants species (Chye et al., *Plant J.* 18: 205-214, 1999).

Upon the isolation of other plant-derived ACBPs, the presence of a functional acyl-CoA-binding domain in these ACBPs can tested in vitro by Lipidex assays using (His)-tagged ACBPs and radiolabeled acyl-CoA esters including, but not limited to, $^{14}$[C]oleoyl-CoA, $^{14}$[C]palmitoyl-CoA, and $^{14}$[C]arachidonyl-CoA as previously described (Chye et al., *Plant Mol. Biol.* 44: 711-721, 2000; Leung et al., *Plant Mol. Biol.* 55: 297-309, 2004; Leung et al., *Planta* 223: 871-881, 2006). Non-radiolabeled acyl-CoA esters can be used in conjunction with radiolabeled acyl-CoA esters to test binding as described in Leung et al., *Planta* 223: 871-881, 2006). (His)-tagged proteins can be generated as described in Examples 3 and 4. The methods for using these (His)-tagged ACBPs in Lipidex assays have already been described in detailed for *Arabidopsis* ACBP 1 to 5 (Chye et al., *Plant Mol. Biol.* 44: 711-721, 2000; Leung et al., *Plant Mol. Biol.* 55: 297-309, 2004; Leung et al., *Planta* 223: 871-881, 2006).

The methods for using (His)-tagged ACBPs in Lipidex assays as described in detailed in Leung et al., Plant Mol. Biol. 55: 297-309, 2004 are illustrated in detail as follows. "In vitro binding assays with [$^{14}$C]palmitoyl-CoA Amersham [$^{14}$C]oleoyl-CoA Amersham or [$^{14}$C]arachidonyl-CoA Moravek were carried out using Lipidex™-1000 (Packard Instrument Co., USA) according to Rasmussen et al. (1990). Assays were performed in triplicates, with blanks, at each concentration of acyl-CoA. Each recombinant ACBP was dissolved in 50 µl of binding buffer (10 mM potassium phosphate buffer, pH 7.4) to a final concentration of 0.8 µM. Each recombinant protein (at 0.2 µM final concentration) was mixed with [$^{14}$C]palmitoyl-CoA, [$^{14}$C]oleoyl-CoA or [$^{14}$C]arachidonyl-CoA, at final acyl-CoA concentrations ranging from 0.2 to 1 µM. The mixtures were incubated for 30 min at 37° C., followed by chilling on ice for 10 min. Then samples were mixed with 400 µl of ice-cold 50% slurry Lipidex™-1000 in binding buffer and kept for 10 min on ice. Samples were centrifuged at 12,000×g for 5 min at 4° C. A 200 µl aliquot of the supernatant was taken for analysis of radioactivity counts using a liquid scintillation counter Type Minaxi Tri-Carb 4000 (Packard). The ratio for the number of moles of bound acyl-CoA molecules to the number of moles of molecules of ACBPs was calculated using the equation of Motulsky and Neubig (1997)."

Example 7

Generation of ACBP1- and ACBP3-Overexpressing Transgenic *Arabidopsis*

Plant transformation vectors pAT31 (35S:ACBP1) and pAT314 (35S:ACBP3) shown in FIGS. 3A-3B were mobilised from *E. coli* into *Agrobacterium tumefaciens* strain LBA4404 by triparental mating (Roger et al., *Plant Molecular Biology Manual* pp. A2: 1-12, 1988), and were subsequently introduced into *Arabidopsis* wild-type plants (ecotype Columbia) using the floral dip method (Clough and Bent, *Plant J.* 16: 735-743, 1998). The transformed $T_0$ seeds were screened on the plant growth medium containing 50 mg/mL kanamycin and the positive transformants were transferred into soil to obtain the $T_1$ population. The positive transformants were further confirmed by PCR using a 35S promoter-specific forward primer 35SB (SEQ ID NO:15) together with reverse gene-specific primers: ML759 (SEQ ID NO:4; for 35S:ACBP1) and ML784 (SEQ ID NO:8; for 35S:ACBP3). RNA gel blot analysis was carried out using the Digoxigenin Northern blot kit (Roche) according to the protocol supplied by the manufacturer that has been also described in Xiao et al. (*Plant Cell* 16:1132-1142, 2004). Briefly, total RNA was extracted from the $T_2$ transformants and 30 µg of total RNA were separated on a 1.5% agarose gel containing 6% formaldehyde and transferred to Hybond N membranes (Amersham). Northern (RNA) blot analysis was performed to detect the 35S:ACBP1 and 35S:ACBP3 transcripts using ACBP1- and ACBP3-specific cDNA probes. To generate probes for Northern blot analyses, specific primers of ACBP1 (ML179, SEQ ID NO:3 and ML759, SEQ ID NO:4) and those of ACBP3 (ML783, SEQ ID NO:7 and ML784, SEQ ID NO:8) were utilized for PCR amplification. The fragments were labeled with the PCR Digoxigenin Probe Synthesis Kit according to the manufacturer's instructions (Roche, Germany). Hybridization and detection were performed according to the standard procedures as advised by the manufacturer (Roche). Western blot analyses were carried out, which is also described by Chye (*Plant Mol. Biol.* 38: 827-838, 1998). Total plant protein was extracted from mature silique-bearing plants. Protein concentrations were determined using the Bio-Rad Protein Assay Kit (Bradford, 1976). Ten µg of total protein was loaded per well in an SDS-PAGE gel. The proteins were electrophoretically transferred to Hybond-C membrane (Amersham) from the SDS-PAGE gel using a Trans-Blot cell (Bio-Rad). Affinity-column purified ACBP1-specific antibodies (Chye, *Plant Mol. Biol.* 38: 827-838, 1998) or GFP-specific antibodies (Invitrogen) were used in Western blot analysis. The ECL Western Blotting Detection Kit (Amersham) was used following the manufacturer's instructions to detect cross-reacting bands.

The $T_3$ stable transformants were tested for Pb(II)-sensitivity and measurement of Pb(II) content. To measure Pb(II) content in ACBP1-overexpressing transgenic *Arabidopsis*, plants were grown on MS medium for 2 to 3 weeks and then transferred into 1 mM Pb(NO$_3$)$_2$ solution for 48 h. The shoots and roots were weighted and collected for Pb(II) content measurement. To measure Pb(II) content in ACBP3-overexpressing transgenic *Arabidopsis*, the shoots of 2-week-old *Arabidopsis* were collected from seedlings germinated and grown on medium containing 0.75 mM Pb(NO$_3$)$_2$. The samples were digested overnight with 11 N HNO$_3$ at 200° C.

as described previously (Lee et al., *Plant Physiol.* 138: 827-836, 2005). After dilution with 0.5 N $HNO_3$, the samples were analyzed using an atomic absorption spectrometer (PERKIN ELMER-AA Spectrometer 3110). Each plant line was tested by harvesting shoot samples from 30 independent plants divided into 6 groups (comprising 5 plants per group), i.e. six replicates were tested for each plant line and each replicate contains 5 plants. The average value for each plant line is derived from three independent experiments.

Example 8

ACBP1-Overexpressing Transgenic Plants are More Tolerant to Pb(II) Stress than Wild Type To substantiate whether ACBP1 confers Pb(II) resistance, ACBP1-overexpressing transgenic plants were generated by *Agrobacterium* transformation (Clough and Bent, *Plant J.* 16: 735-743, 1998). To this end, the ACBP1 full-length cDNA was cloned into binary vector pBI121 in which ACBP1 is expressed from the CaMV 35S promoter. The resultant plant transformation vector pAT31 (FIG. 3A) was subsequently introduced into wild-type (Col-0) *Arabidopsis* plants using *Agrobacterium*-mediated transformation by the floral dip approach (Clough and Bent, *Plant J.* 16: 735-743, 1998). Three independent $T_2$ transgenic lines were identified to over-produce ACBP1 mRNA in RNA gel blot analysis (FIG. 4A). Among them, two lines (designated ACBP1 ox-3 and ACBP1 ox-5) showed a 3:1 (resistant/sensitive) segregation ratio in the $T_2$ population grown on growth medium containing the selective antibiotic kanamycin, indicating that they contain only one copy of the 35S::ACBP1 transgene. The ACBP1 protein levels in wild type, ACBP1 ox-3 and ACBP1 ox-5 were further confirmed by Western blot analyses using ACBP1-specific antibodies (FIG. 4B) and their resultant $T_3$ stable transgenic plants hence selected for Pb(II) treatment.

Wild-type (Col-0) and the $T_3$ 35S::-ACBP1 transgenic plants (ACBP1 ox-3 and ACBP1 ox-5) were grown on MS medium for 3 days after germination and then transferred to MS medium and MS medium containing 0.75 mM $Pb(NO_3)_2$ for vertically growth. As presented in FIG. 4C, although the growth rates of wild type and $T_3$ transgenic plants were similar seventeen days after germination on MS (Murashige and Skoog, *Physiol. Plant.* 15: 473-497, 1962) medium (FIG. 4C), growth of wild type lagged behind ACBP1-transformed lines on MS supplemented with 0.75 mM $Pb(NO_3)_2$. Data (FIG. 4D) revealed that the relative root lengths of the two transgenic lines ACBP1 ox-3 and ACBP1 ox-5 grown on Pb(1)-containing medium were 40.0±2.0% and 36.2±2.3%, respectively, of similar plants grown in MS medium. These values were significantly (P<0.05) higher than those of wild type (23.7±2.1%). Also, the relative fresh weights (FIG. 4E) of the ACBP1 ox-3 and ACBP1 ox-5 transgenic lines grown in the presence of Pb(II) were respectively, 1.6- and 1.5-fold higher in shoots, and 1.8- and 1.4-fold higher in roots, than wild type. These changes in fresh weights, expressed as a percentage to that obtained from plants grown in the absence of Pb(II), are significant (P<0.05).

Example 9

ACBP3-Overexpressing Transgenic Plants are More Tolerant to Pb(II) Stress than Wild Stress To substantiate whether ACBP3 confers Pb(II) resistance, ACBP3-overexpressing transgenic plants were generated by *Agrobacterium* transformation (Clough and Bent, *Plant J.* 16: 735-743, 1998). To this end, the ACBP3 full-length cDNA was cloned into binary vector pBI-GFP, a pBI121 derivative obtained by replacement of the GUS gene with eGFP (Shi et al., *Plant Cell* 17: 2340-2354, 2005), to generate plasmid pAT314, in which ACBP3 is expressed from the CaMV 35S promoter. Plant transformation vector pAT314 (FIG. 3B) was subsequently introduced into wild-type (Col-0) *Arabidopsis* plants using *Agrobacterium*-mediated transformation by the floral dip approach (Clough and Bent, *Plant J.* 16: 735-743, 1998). Three independent $T_2$ transgenic lines were identified to over-produce ACBP3-GFP mRNA in RNA gel blot analysis (FIG. 5A). Among them, all three lines (designated ACBP3 ox-2, ACBP3 ox-9 and ACBP3 ox-11) showed a 3:1 (resistant/sensitive) segregation ratio in the $T_2$ population grown on growth medium containing the selective antibiotic kanamycin, indicating that they contain only one copy of the 35S::ACBP3 transgene. The ACBP3-GFP fusion protein levels in wild type, ACBP3 ox-2, ACBP3 ox-9 and ACBP1 ox-11 were further confirmed by Western blot analyses using the GFP-specific antibodies (FIG. 5B) and their resultant $T_3$ stable transgenic plants were hence selected for Pb(II) treatment.

Figure 5E:
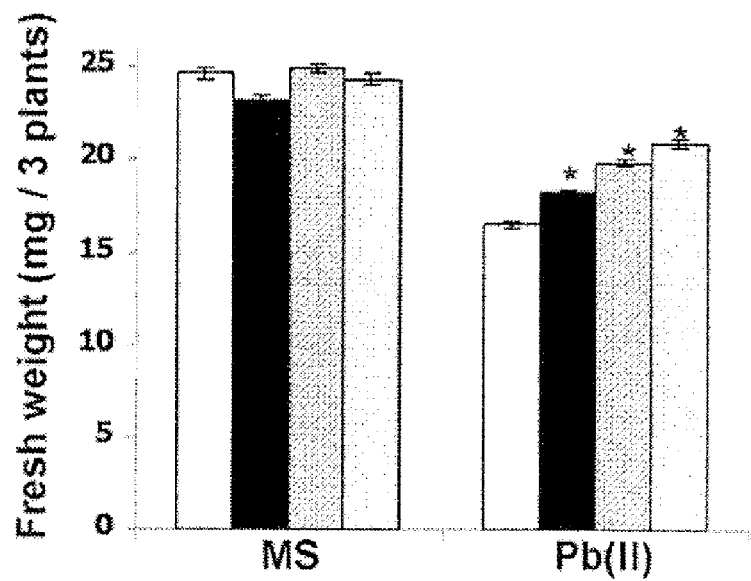

Although wild type (Col-0) and the $T_3$ 35S::ACBP3 transgenic plants (ACBP3 ox-2. ACBP3 ox-9 and ACBP3 ox-11) showed similar growth on MS medium, only growth of wild type was inhibited when these lines were cultured on medium containing 0.75 mM $Pb(NO_3)_2$ for 3 weeks (FIG. 5C). The ACBP3 ox-2, ACBP3 ox-9 and ACBP3 ox-11 transformed plants clearly exhibited better growth than wild type upon $Pb(NO_3)_2$ treatment (FIG. 5C). Quantitative analyses also showed that the root lengths (FIG. 5D) and fresh weights (FIG. 5E) of wild type, ACBP3 ox-2, ACBP3 ox-9 and ACBP3 ox-11 transformed plants did not show significant differences in MS medium but the root lengths of the three independent transgenic lines were longer (16.8±0.12, 17.8±0.12 and 14.8±0.12 mm, respectively) compared to wild type (7.2±0.08 mm). Also, the fresh weights of the ACBP3 ox-2, ACBP3 ox-9 and ACBP3 ox-11 transformed lines were 1.1-, 1.2- and 1.27-fold higher than wild type in Pb(II)-containing medium (FIG. 5E).

Example 10

Greater Accumulation of Pb (II) in ACBP-Overexpressing Transgenic Plants

We further investigated whether ACBP-mediated resistance to Pb(II) was due to Pb(II) extrusion like AtPDR12-overexpressing *Arabidopsis* plants (Lee et al., *Plant Physiol.* 138: 827-836, 2005) or translocation that would result in Pb(II) accumulation in plant cells, thus resembling the overexpression of AtATM3 and YCF1 in transgenic plants (Kim et al., *Plant Physiol.* 140: 922-932, 2006; Song et al., *Nat. Biotech.* 21: 914-919, 2003).

To measure Pb(II) content in the ACBP1-overexpressing transgenic plants, wild type (Col-0), ACBP1 ox-3 and ACBP1 ox-5 lines were grown on MS for 3 weeks before seedlings were transferred to immerse roots in 1 mM $Pb(NO_3)_2$ for 48 h. The plants were washed three times in distilled water and blotted dry. Root and shoot samples were weighed and subsequently digested overnight with 11 N $HNO_3$ at 200° C. After dilution with 0.5 N $HNO_3$, the samples were analyzed using an atomic absorption spectrometer (PERKIN ELMER-AA Spectrometer 3110). As shown in FIG. 6A, When the Pb(II) contents of wild type and transgenic lines were normalized on a per-plant basis, ACBP1 ox-3 and ACBP1 ox-5 lines showed 3.4- and 2.9-fold increases over wild type, respectively, in shoot Pb(II) content (P<0.001) with little variation in roots. When the Pb(II) contents in wild-type and transgenic *Arabidopsis* were compared on the per-fresh weight basis, ACBP1 ox-3 and ACBP1 ox-5 lines showed 1.9- and 2.2-fold increases, respectively, in shoot Pb(II) content (P<0.05; FIG. 6B), confirming that the overexpression of ACBP1 resulted in Pb(II) accumulation in shoots.

The Pb(II) contents in the ACBP3-overexpressing transgenic plants were also measured. Wild type (Col-0) and ACBP3 ox-11 line were germinated and grown on MS containing 0.75 mM Pb(NO$_3$)$_2$ for 2 weeks before shoots were harvested for measurement of Pb(II) content. FIG. 7A shows that the ACBP3-overexpressing ACBP3 ox-11 line also accumulates greater Pb(II) content (39.1±0.68 ppm/1 plant) than wild type (36.1±0.6 ppm/1 plant). When the Pb(II) content of wild-type and transgenic *Arabidopsis* were compared on the per-fresh weight basis, ACBP3 ox-11 showed 1.4-fold increase over wild type in shoot Pb(II) content (P<0.05; FIG. 7B), confirming that the overexpression of ACBP3 also resulted in Pb(II) accumulation in shoots.

Example 11

Applications in the Use of ACBP Constructs in Plastid Transformation

Figure 9A:
Figure 9B:
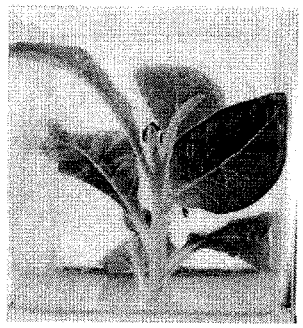
Figure 9C:
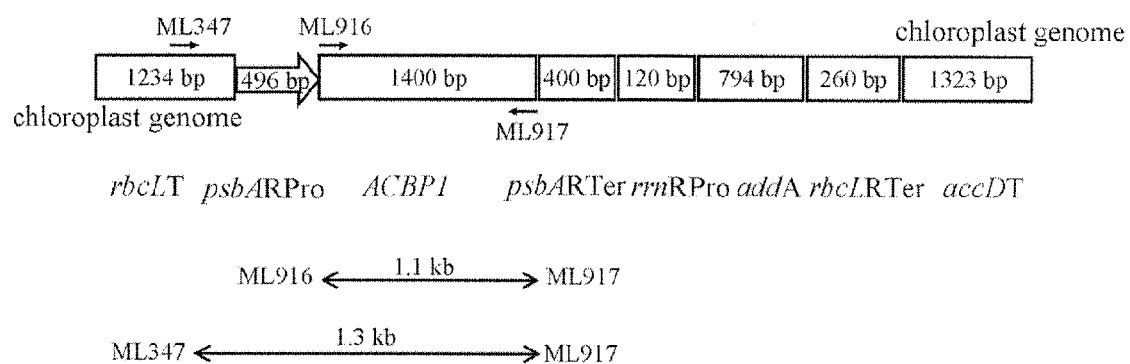
Figure 9D:
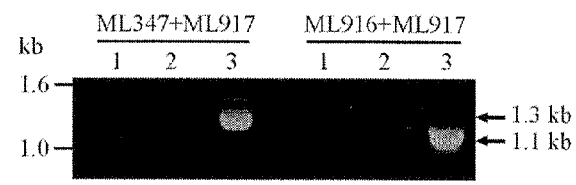

The promoters used for plastid transformation include strong and constitutive promoters in plastid expression including the psbA promoter (the psbA gene encodes the photosystem II 32 kD protein) and the 16S rRNA operon (rrn) promoter, or modifications thereof of these promoters which have enhanced expression (Suzuki et al., 2003, *Plant Cell* 15: 195-205). In a specific embodiment, each plastid transformation construct containing ACBP-encoding sequences was cloned into plastid transformation vector pMLV-HisA (Li et al. *Exp. Biol. Med.* 231: 1346-1352, 2006) shown in FIG. 8A, to yield plastid transformation vectors such as pAT385 (FIG. 8B) for introduction by particle gun bombardment into plant cells (Staub and Maliga, *Plant J.* 6: 547-553, 1994). An example of tobacco plastid transformation using vector pAT385 is illustrated in FIGS. 9A-9B and the molecular analyses of plants after transformation is shown in FIGS. 9C-9D.

Example 12

Generation of Plants Expressing ACBPs

According to an embodiment of the present invention, a wide variety of plants and plant cell systems can be engineered for the desired physiological and agronomic characteristics described herein using the nucleic acid constructs of the present invention by various transformation methods known in the art, including *Agrobacterium*-mediated transformation (Horsch et al., *Science* 227: 1227-1231, 1985) or plastid transformation (Staub and Maliga, *Plant J.* 6: 547-553, 1994). In preferred embodiments, target plants and plant cells for engineering include, but are not limited to, those monocotyledonous and dicotyledonous plants, such as crops including grain crops (for example, wheat, maize, rice, millet, barley), tobacco, fruit crops (for example, tomato, apple, pear, strawberry, orange), forage crops (for example, alfalfa), root vegetable crops (for example, carrot, potato, sugar beets, yam), leafy vegetable crops (for example, lettuce, spinach); flowering plants (for example, petunia, rose, chrysanthemum), conifers and pine trees (for example, pine fir, spruce); plants used in phytoremediation (for example, heavy metal accumulating plants); oil crops (for example, sunflower, rape seed); and plants used for experimental purposes (for example, *Arabidopsis*).

According to another embodiment of the present invention, desired plants may be obtained by engineering one or more of the vectors expressing ACBPs as described herein into a variety of plant cell types, including but not limited to, protoplasts, tissue culture cells, tissue and organ explants, pollens, embryos, as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant and progeny thereof (including the immediate and subsequent generations) via sexual or asexual reproduction or growth. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the alt.

According to another embodiment of the present invention, tissue-specific promoters may be used to target the expression of ACBPs in roots or leaves so that an edible plant part is free from heavy metal accumulation. Examples of tissue-specific promoters include those encoding rbsC (Coruzzi et al., *EMBO J.* 3:1671-1697, 1984) for leaf-specific expression and SAHH or SHMT (Sivanandan et al., *Biochimica et Biophysica Acta* 1731:202-208, 2005) for root-specific expression. Another exemplary root-specific promoter is taught by Ekramoddoullah et al., U.S. Pat. No. 7,285,656 B2. Also, the Cauliflower Mosaic Virus (CaMV) 35S promoter has been reported to have root-specific and leaf-specific modules in its promoter region (Benfey et al., *EMBO J.* 8:2195-2202, 1989). Other tissue-specific promoters are well known and widely available to those of ordinary skill in the art. Further, a wide variety of constitutive or inducible promoters are also well known and widely available to those of ordinary skill in the art.

A transformed plant cell, callus, tissue, or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the vector of the present invention. Such selection and screening methodologies are well known to those skilled in the art.

Physical and biochemical methods may also be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art. In a specific embodiment, the selectable marker gene nptII, which specifies kanamycin-resistance, is used in nuclear transformation.

Examples of plants are monocots, dicots, crop plants (i.e., any plant species grown for purposes of agriculture, food production for animals including humans, plants that are typically grown in groups of more than about 10 plants in order to harvest the entire plant or a part of the plant, for example, a fruit, a flower or a crop, for example, tobacco, grain, that the plants bear, etc.), trees (i.e., fruit trees, trees grown for wood production, trees grown for decoration, etc.), flowers of any kind (i.e., plants grown for purposes of decoration, for example, following their harvest), cactuses. Further examples of plants in which the ACBPs may be expressed include Viridiplantae, Streptophyta, Embryophyta, Tracheophyta, Euphyllophytes, Spermatophyta, Magnoliophyta, Liliopsida, Commelimidae, Poales, Poaceae, *Oryza, Oryza sativa, Zea, Zea mays, Hordeum, Hordeum vulgare, Triticum, Triticum aestivum*, Eudicotyledons, Core eudicots, Asteridae, Euasterids, Rosidae, Eurosids II, Brassicales, Brassicaceae, *Arabidopsis*, Magnoliopsida, Solananae, Solanales, Solanaceae, *Solanum*, and *Nicotiana*. Thus, the embodiments of the invention have used over a broad range of plants including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum, Vicia, Vitis, Vigna*, and *Zea*.

All patents, patent applications, provisional applications, and publications referred to or cited herein are incorporated by reference in their entirety, including all figures and tables, to the extent they are not inconsistent with the explicit teachings of this specification.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. Altschul S F, Gish W, Miller W, Myers E W and Lipman D J. 1990. Basic local alignment search tool. J. Mol. Biol. 215: 403-410.
2. Batzer M A. 1997. Computer Methods for Macromolecular Sequence Analysis. Methods in Enzymology, vol. 266. ed. Doolittle, Academic Press, Inc., a division of Harcourt Brace & Co., San Diego, Calif., USA.
3. Benfey P N, Ren L and Chua N H. 1989. The CaMV 35S enhancer contains at least two domain which can confer different developmental and tissue-specific expression patterns. EMBO J. 8:2195-2202.
4. Bradford M M. 1976. A rapid and sensitive method for the quantitation of microgram quantities of protein utilizing the principle of protein-dye binding. Anal. Biochem. 72: 248-254.
5. Chiang L W, Kovari I, Howe M M. 1993. Mutagenic oligonucleotide-directed PCR amplification (Mod-PCR): an efficient method for generating random base substitution mutations in a DNA sequence element. PCR Methods Appl. 2: 210-217.
6. Chye M L. 1998. *Arabidopsis* cDNA encoding a membrane-associated protein with an acyl-CoA-binding domain. Plant Mol. Biol. 38: 827-838.
7. Chye M L, Huang B Q and Zee S Y. 1999. Isolation of a gene encoding *Arabidopsis* membrane-associated acyl-CoA-binding protein and immunolocalization of its gene product. Plant J. 18: 205-214.
8. Chye M L, Li H Y and Yung M H. 2000. Single amino acid substitutions at the acyl-CoA-binding domain interrupt $^{14}$[C]palmitoyl-CoA binding of ACBP2, an *Arabidopsis* acyl-CoA-binding protein with ankyrin repeats. Plant Mol. Biol. 44: 711-721.
9. Clough S J and Bent A F. 1998. Floral dip: a simplified method for *Agrobacterium*-mediated transformation of *Arabidopsis thaliana*. Plant J. 16: 735-743.
10. Coruzzi G, Broglie R, Edwards C and Chua N H. 1984. Tissue-specific and light-regulated expression of a pea nuclear gene encoding the small subunit of ribylose-1.5-bisphosphate carboxylase. EMBO J. 3:1671-1679.
11. Dhankher O P, Li Y, Rosen B O, Shi J, Salt D, Senecoff J F, Sashti N A and Meagher R B. 2002. Engineering tolerance and hyperaccumulation of arsenic in plants by combining arsenate reductase and gainma-glutamylcysteine synthetase expression. Nature Biotech. 20: 1140-1146.
12. Dykema P E, Sipes P R, Marie A, Biermann B J, Crowell D N and Randall S K. 1999. A new class of proteins capable of binding transition metals. Plant Mol. Biol. 41: 139-150.
13. Engeseth N J, Pacovsky R B, Newman T and Ohlrogge J B. 1996. Characterization of an acyl-CoA-binding protein from *Arabidopsis thaliana*. Arch. Biochem. Biophys. 331: 55-62.
14. Faergeman N J and Knudsen J. 1997. Role of long-chain fatty acyl-CoA esters in the regulation of metabolismn and in cell signalling. Biochem. J. 323: 1-12.
15. Funaba M and Mathews L S. 2000. Identification and characterization of constitutively active Smad2 mutants: evaluation of formation of Smad complex and subcellular distribution. Mol. Endocrinol. 14: 1583-1591.
16. Greener et al. 1995. An Efficient Random Mutagenesis Technique Using an *E. coli* Mutator Strain. Methods in Molecular Biology, 57:375-385.
17. Horsch R B, Fry J E, Hoffmann N L, Eichholtz D, Rogers S G and Fraley R T. 1985. A Simple and General-Method for Transferring Genes into Plants. Science 227: 1229-1231.
18. Kim D Y, Bovet L, Kushnir S, Noh E W, Martinoia E and Lee Y. 2006. AtATM3 is involved in heavy metal resistance in *Arabidopsis*. Plant Physiol. 140: 922-932.
19. Kragelund B B, Knudsen J and Poulsen F M. 1999. Acyl-coenzyme A binding protein (ACBP). Biochim. Biophy. Acta 1441: 150-161.
20. Kramer U. 2005. Phytoremediation: novel approaches to cleaning up polluted soils. Curr. Opin. Biotech. 16: 133-141.
21. Laeimmli U K. 1970. Cleavage of structural proteins during the assembly of the head of bacteriophage T4. Nature 227: 680-685.

22. Layne E. 1957. Spectrophotometric and turbidimetric methods for measuring protein. Methods in Enzymology 3: 447-454.
23. Lee M, Lee K, Lee J, Nob E W and Lee Y. 2005. AtPDR12 contributes to lead resistance in *Arabidopsis*. Plant Physiol. 138: 827-836.
24. Leung K C, Li H Y, Mishra G and Chye M L. 2004. ACBP4 and ACBP5, novel *Arabidopsis* acyl-CoA-binding proteins with ketch motifs that bind oleoyl-CoA. Plant Mol. Biol. 55: 297-309.
25. Leung K C, Li H Y, Xiao S, Tse M H and Chye M L. 2006. *Arabidopsis* ACBP3 is an extracellularly targeted acyl-CoA-binding protein. Planta 223: 871-881.
26. Li H Y and Chye M L. 2003. Membrane localization of *Arabidopsis* acyl-CoA-binding protein ACBP2. Plant Mol. Biol. 51: 483-492.
27. Li H Y, Ramalingam S and Chye M L. 2006. Accumulation of recombinant SARS-CoV spike protein in plant cytosol and chloroplasts indicate potential for development of plant-derived oral vaccines. Exp. Biol. Med. 231: 1346-1352.
28. Murashige T and Skoog F. 1962. A revised medium for rapid growth and bio assays with tobacco tissue cultures. Physiol. Plant. 15: 473-497.
29. Needleman S B and Wunsch C D. 1970. A general method applicable to the search for similarities in the amino acid sequence of two proteins. J. Mol. Biol. 48: 443-453.
30. Nitz I, Doring F, Schreznmeir J and Burwinkel B. 2005. Identification of new acyl-CoA-binding protein transcripts in human and mouse. Int. J. Biochem. Cell Biol. 37: 2395-2405.
31. Powell K. 2002. Genes improve green cleaning. Nature doi: 10.1038/news021001-14.
32. Rasmussen J T, Borchers T and Knudsen J. 1990. Comparison of the binding affinities of acyl-CoA-binding protein and fatty-acid-binding protein for long-chain acyl-CoA esters. Biochem. J. 265: 849-855.
33. Rogers G S, Klee H, Horsch R B and Fraley R T. 1988. Use of cointegrating Ti plasmid vectors. In Gelvin S B, Schilperoort R A and Verma D P S. (eds.) Plant Molecular Biology Manual pp A2: 1-12. Kluwer Academic Publishers.
34. Sambrook J, Fritsch E F and Maniatis T. 1989. Molecular Cloning: A Laboratory Manual. Second Edition. Cold Spring Harbor Laboratory Press, Cold Spring Harbor.
35. Sambrook, J. and Russell, W. 2001. *Molecular Cloning: A Laboratory Manual*, Third Edition, Cold Spring Harbor Laboratory Press, Cold Spring Harbor.
36. Shi D Q, Liu J, Xiang Y H, Ye D, Sundaresan V, and Yang W C. 2005. SLOW WALKER1, essential for gametogenesis in *Arabidopsis*, encodes a WD40 protein involved in 18S ribosomal RNA biogenesis. Plant Cell 17:2340-2354.
37. Shpaer E G. 1997. GeneAssist. Smith-Waterman and other database similarity searches and identification of motifs. Meth. Mol. Biol. 70: 173-187.
38. Sivanandan C, Sujatha T P, Prasad A M, Resminath R, Thakare D R, Bhat T A R and Srinivasan R. 2005. T-DNA tagging and characterization of a cryptic root-specific promoter in *Arabidopsis*. Biochimica et Biophysica Acta 1731:202-208.
39. Smith D R, Kahng M W, Quintanilla-Vega B and Fowler B A. 1998. High-affinity renal lead-binding proteins in environmentally-exposed humans. Chem. Biol. Interact. 115: 39-52.
40. Song W Y, Ju Sohn E, Martinoia E, Jik Lee Y, Yang Y Y, Jasinski M, Forestier C, Hwang, I and Lee Y. 2003. Engineering tolerance and accumulation of lead and cadmium in transgenic plants. Nat. Biotech. 21: 914-919.
41. Staub J M, and Maliga P. 1994. Translation of Psba Messenger-Rna Is Regulated by Light Via the 5'-Untranslated Region in Tobacco Plastids. Plant J. 6: 547-553.
42. Stemmer W P. 1994. DNA shuffling by random fragmentation and reassembly: in vitro recombination for molecular evolution. Proc. Natl. Acad. Sci. USA. 91: 10747-10751.
43. Suzuki J Y, Sriraman P, Svab Z and Maliga P. 2003. Unique architecture of the plastid ribosomal RNA operon promoter recognized by the multisubunit RNA polymerase in tobacco and other higher plants. Plant Cell 15: 195-205.
44. Swinnen J V, Esquenet M, Rosseels J, Claessens F, Rombauts W, Heyns W and Verhoeven G. 1996. A human gene encoding diazepam-binding inhibitor/acyl-CoA-binding protein:transcription and hormonal regulation in the androgen-sensitive human prostatic adenocarcinoma cell line LNCaP. DNA Cell Biol. 15: 197-208.
45. Stemple D L. 2004. TILLING-a high-throughput harvest for func-tional genomics. Nature Reviews, 5: 1-7.
46. Xiao S, Dai L, Liu F, Wang Z, Peng W and Xie D. 2004. COS1: an *Arabidopsis* coronatine insensitive1 suppressor essential for regulation of jasmonate-mediated plant defense and senescence. Plant Cell 16: 1132-1142.

What is claimed is:

1. A method of phytoremediation of an environment contaminated with a heavy metal comprising
    selecting an environment contaminated with a heavy metal; and growing, in that environment, an organism stably transformed to over-express, as compared to a non-transformed organism of the same type, a nucleic acid encoding a plant-derived acyl-CoA-binding protein (ACBP) or a variant of a plant-derived ACBP that binds at least one heavy metal, wherein the organism is a plant or microbe and the plant-derived ACBP is an *Arabidopsis* ACBP selected from the group consisting of ACBP 1 (SEQ ID NO: 27), ACBP2 (SEQ ID NO: 28), ACBP3 (SEQ ID NO: 29), ACBP4 (SEQ ID NO: 30), ACBP5 (SEQ ID NO: 31), and ACBP6 (SEQ ID NO: 26), and wherein the polynucleotide encoding said *Arabidopsis* ACBP or variant thereof will hybridize with a polynucleotide encoding said *Arabidopsis* ACBP under stringent hybridization conditions with a final wash of 0.1×SSC at 65° C.; whereby an amount of heavy metal is removed from the environment.

2. The method according to claim 1, wherein the transformed organism is a transformed plant.

3. The method according to claim 1, wherein said nucleic acid is in the nucleus of the transformed plant.

4. The method according to claim 1, wherein said nucleic acid is in a plastid of the transformed plant.

5. The method according to claim 1, wherein the heavy metal is one or more of lead, copper, cadmium, nickel, mercury, arsenic, selenium, strontium and zinc.

6. The method according to claim 1, wherein said ACBP is ACBP1, ACBP2, ACBP3, or ACBP4.

7. The method according to claim 6, wherein the ACBP is ACBP1.

8. The method according to claim 2, wherein the transformed plant is *Arabidopsis*.

9. The method according to claim 2, wherein the recombinant vector contains a nucleic acid that targets the ACBP to specific tissues within the plant which can be pruned off to remove the heavy metal contaminant without destroying the whole plant.

10. The method according to claim 1, wherein the transformed organism is a transformed microbe.

11. A method for monitoring/detecting the presence of contaminating metal in an environment comprising
    selecting an environment to be tested or monitored for the presence of a contaminating metal; growing, in that environment, a plant stably transformed to express a plant-derived ACBP or a variant thereof that binds at least one heavy metal wherein the plant derived ACBP is an *Arabidopsis* ACBP selected from the group consisting of ACBP1 (SEQ ID NO: 27), ACBP2 (SEQ ID NO: 28), ACBP3 (SEQ ID NO: 29), ACBP4 (SEQ ID NO: 30), ACBP5 (SEQ ID NO: 31), and ACBP6 (SEQ ID NO: 26), and wherein the polynucleotide encoding said *Arabidopsis* ACBP or variant thereof will hybridize with a polynucleotide encoding said *Arabidopsis* ACBP under stringent hybridization conditions with a final wash of 0.1×SSC at 65° C.; and testing at least a portion of said plant for the presence of a contaminating metal, whereby presence or absence of the contaminating metal in the environment is indicated.

12. The method according to claim 11, wherein the ACBP is ACBP1, ACBP2, ACBP3, or ACBP4.

13. A cell stably transformed to express a nucleic acid encoding a plant-derived acyl-CoA-binding protein selected from the group consisting of ACBP1 (SEQ ID NO: 27), ACBP2 (SEQ ID NO: 28), ACBP3 (SEQ ID NO: 29), ACBP4 (SEQ ID NO: 30), ACBP5 (SEQ ID NO: 31), and ACBP6 (SEQ ID NO: 26); wherein the transformed cell is a plant cell or microbe and wherein the transformed cell overexpresses said nucleic acid and is able to uptake a heavy metal from its environment.

14. The cell according to claim 13, which is a transformed microbe.

15. The cell according to claim 14, which is an *E. coli*.

16. The cell according to claim 13, which is a transformed plant cell.

17. The cell according to claim 16, wherein the plant cell is an *Arabidopsis*.

18. A plant comprising the cell of claim 16.

19. The plant according to claim 18, wherein the plant is an *Arabidopsis*.

20. The cell according to claim 13, wherein the plant-derived acyl-CoA-binding protein is ACBP1, ACBP2, ACBP3, or ACBP4.

21. The cell according to claim 20, wherein the ACBP is ACBP1.

* * * * *

UNITED STATES PATENT AND TRADEMARK OFFICE
CERTIFICATE OF CORRECTION

PATENT NO.        : 7,880,053 B2
APPLICATION NO.   : 12/062077
DATED             : February 1, 2011
INVENTOR(S)       : Mee Len Chye et al.

It is certified that error appears in the above-identified patent and that said Letters Patent is hereby corrected as shown below:

Column 10,
Line 14, "CAAG-3)" should read --CAAG-3')--.

Column 15,
Line 29, "nebi.nlm.nih.gov/BLAST" should read --ncbi.nlm.nih.gov/BLAST--.

Column 22,
Lines 2-3, "nucleotides u stream from" should read --nucleotides upstream from--.
Line 44,
" (MRGSHHHHHHGMASMTGGQQMGRDLYDDDDIDRWIRPRDLQLVPWNSR), "
should read
-- (MRGSHHHHHHGMASMTGGQQMGRDLYDDDDKDRWIRPRDLQLVPWNSR), --.

Column 24,
Line 13, "(Qiagen, Valebcia, CA, USA)" should read --(Qiagen, Valencia, CA, USA)--.

Column 26,
Line 33,
" LxxLxxAxxGxxxxxxPxxxxxxxxxKWxxWxxxxxxxxxEAM " should read
-- LxxLxxxAxxGxxxxxxPxxxxxxxxxKWxxWxxxxxxxxxEAM --.
Line 56, "able detect" should read --able to detect--.

Column 27,
Line 31, "can tested" should read --can be tested--.

Column 29,
Line 37, "T$_3$ *35S::-ACBP1* transgenic" should read --T$_3$ *35S::ACBP1* transgenic--.
Line 49, "Pb(1)-containing" should read --Pb(II)-containing--.

Signed and Sealed this
Seventh Day of June, 2011

David J. Kappos
*Director of the United States Patent and Trademark Office*

Column 32,
Line 22, "skilled in the alt." should read --skilled in the art.--.

Column 34,
Line 32, "reductase and gainma-glutamylcysteine" should read --reductase and gamma-glutamylcysteine--.
Line 42, "regulation of metabloismn" should read --regulation of metabolism--.
Line 65, "21. Laeimmli" should read --21. Laemmli--.

Column 35,
Line 4, "Lee J, Nob E W and" should read --Lee J, Noh EW and--.
Line 9, "with ketch motifs" should read --with kelch motifs--.

Column 36,
Line 42, "for func-tional genomics." should read --for functional genomics.--.

SEQUENCE LISTING

```
<160> NUMBER OF SEQ ID NOS: 31

<210> SEQ ID NO 1
<211> LENGTH: 31
<212> TYPE: DNA
<213> ORGANISM: Arabidopsis

<400> SEQUENCE: 1
atatggatcc cacgcgttgt cctcgtcttc t                                    31

<210> SEQ ID NO 2
<211> LENGTH: 24
<212> TYPE: DNA
<213> ORGANISM: Arabidopsis
```

-continued

```
<400> SEQUENCE: 2
aatatatcat cttgaattca actg                                          24

<210> SEQ ID NO 3
<211> LENGTH: 38
<212> TYPE: DNA
<213> ORGANISM: Arabidopsis

<400> SEQUENCE: 3
cgggatccga aaatgtcaat ctttggtttg atcttcgc                           38

<210> SEQ ID NO 4
<211> LENGTH: 25
<212> TYPE: DNA
<213> ORGANISM: Arabidopsis

<400> SEQUENCE: 4
gtctacaatt ggaatccttc ttctc                                         25

<210> SEQ ID NO 5
<211> LENGTH: 17
<212> TYPE: DNA
<213> ORGANISM: Arabidopsis

<400> SEQUENCE: 5
tcaaggggag agtttcc                                                  17

<210> SEQ ID NO 6
<211> LENGTH: 17
<212> TYPE: DNA
<213> ORGANISM: Arabidopsis

<400> SEQUENCE: 6
cgtcacccag aggagtc                                                  17

<210> SEQ ID NO 7
<211> LENGTH: 29
<212> TYPE: DNA
<213> ORGANISM: Arabidopsis

<400> SEQUENCE: 7
ctctcgagat ggtggagaac gatttgagt                                     29

<210> SEQ ID NO 8
<211> LENGTH: 32
<212> TYPE: DNA
<213> ORGANISM: Arabidopsis

<400> SEQUENCE: 8
acgagctcac atcatactct tagggaatac ca                                 32

<210> SEQ ID NO 9
<211> LENGTH: 28
<212> TYPE: DNA
<213> ORGANISM: Arabidopsis

<400> SEQUENCE: 9
agctcgagat ggctatgcct agggcaac                                      28

<210> SEQ ID NO 10
<211> LENGTH: 28
<212> TYPE: DNA
<213> ORGANISM: Arabidopsis
```

<400> SEQUENCE: 10
cggagctcaa tggcattacc ggaccaaa                                28

<210> SEQ ID NO 11
<211> LENGTH: 30
<212> TYPE: DNA
<213> ORGANISM: Arabidopsis

<400> SEQUENCE: 11
cggatccaat ggctcacatg gtgagagcag                              30

<210> SEQ ID NO 12
<211> LENGTH: 30
<212> TYPE: DNA
<213> ORGANISM: Arabidopsis

<400> SEQUENCE: 12
cgaattctca tgggcactca tgttttaggc                              30

<210> SEQ ID NO 13
<211> LENGTH: 21
<212> TYPE: DNA
<213> ORGANISM: Arabidopsis

<400> SEQUENCE: 13
gctcgaagac gatcagatac c                                       21

<210> SEQ ID NO 14
<211> LENGTH: 21
<212> TYPE: DNA
<213> ORGANISM: Arabidopsis

<400> SEQUENCE: 14
agaaagagct ctcagctcgt c                                       21

<210> SEQ ID NO 15
<211> LENGTH: 25
<212> TYPE: DNA
<213> ORGANISM: Arabidopsis

<400> SEQUENCE: 15
caatcccact atccttcgca agacc                                   25

<210> SEQ ID NO 16
<211> LENGTH: 27
<212> TYPE: DNA
<213> ORGANISM: Arabidopsis

<400> SEQUENCE: 16
tggggcccat ggctgattgg tatcagc                                 27

<210> SEQ ID NO 17
<211> LENGTH: 29
<212> TYPE: DNA
<213> ORGANISM: Arabidopsis

<400> SEQUENCE: 17
gcatcgatct ttgacacaca attttaaag                               29

<210> SEQ ID NO 18
<211> LENGTH: 22
<212> TYPE: DNA

<213> ORGANISM: Arabidopsis

<400> SEQUENCE: 18
cacacaaatc ggtagagctt at                                              22

<210> SEQ ID NO 19
<211> LENGTH: 48
<212> TYPE: PRT
<213> ORGANISM: Arabidopsis

<400> SEQUENCE: 19

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Ile Arg Pro Arg Asp Leu Gln Leu Val Pro Trp Asn Ser Arg
        35                  40                  45

<210> SEQ ID NO 20
<211> LENGTH: 37
<212> TYPE: DNA
<213> ORGANISM: Arabidopsis

<400> SEQUENCE: 20
cgggatccga aaatgtcgct aatctctatc ctcctcg                              37

<210> SEQ ID NO 21
<211> LENGTH: 20
<212> TYPE: DNA
<213> ORGANISM: Arabidopsis

<400> SEQUENCE: 21
atgggtgatt gggctcaact                                                 20

<210> SEQ ID NO 22
<211> LENGTH: 20
<212> TYPE: DNA
<213> ORGANISM: Arabidopsis

<400> SEQUENCE: 22
ttagtctgcc tgctttgcag                                                 20

<210> SEQ ID NO 23
<211> LENGTH: 20
<212> TYPE: DNA
<213> ORGANISM: Arabidopsis

<400> SEQUENCE: 23
ttctccgtct tacaccgatt                                                 20

<210> SEQ ID NO 24
<211> LENGTH: 20
<212> TYPE: DNA
<213> ORGANISM: Arabidopsis

<400> SEQUENCE: 24
cttgatgagg catttagtgc                                                 20

<210> SEQ ID NO 25
<211> LENGTH: 21
<212> TYPE: DNA
<213> ORGANISM: Arabidopsis

<400> SEQUENCE: 25
tgggtaaagc tgagtaacaa g                                                                                          21

<210> SEQ ID NO 26
<211> LENGTH: 92
<212> TYPE: PRT
<213> ORGANISM: Arabidopsis

<400> SEQUENCE: 26

```
Met Gly Leu Lys Glu Glu Phe Glu Glu His Ala Glu Lys Val Asn Thr
1               5                   10                  15

Leu Thr Glu Leu Pro Ser Asn Glu Asp Leu Leu Ile Leu Tyr Gly Leu
            20                  25                  30

Tyr Lys Gln Ala Lys Phe Gly Pro Val Asp Thr Ser Arg Pro Gly Met
        35                  40                  45

Phe Ser Met Lys Glu Arg Ala Lys Trp Asp Ala Trp Lys Ala Val Glu
    50                  55                  60

Gly Lys Ser Ser Glu Glu Ala Met Asn Asp Tyr Ile Thr Lys Val Lys
65                  70                  75                  80

Gln Leu Leu Glu Val Ala Ala Ser Lys Ala Ser Thr
                85                  90
```

<210> SEQ ID NO 27
<211> LENGTH: 338
<212> TYPE: PRT
<213> ORGANISM: Arabidopsis

<400> SEQUENCE: 27

```
Met Ala Asp Trp Tyr Gln Leu Ala Gln Ser Ile Ile Phe Gly Leu Ile
1               5                   10                  15

Phe Ala Tyr Leu Leu Ala Lys Leu Ile Ser Ile Leu Leu Ala Phe Lys
            20                  25                  30

Asp Glu Asn Leu Ser Leu Thr Arg Asn His Thr Thr Gln Ser Glu Tyr
        35                  40                  45

Glu Asn Leu Arg Lys Val Glu Thr Leu Ile Gly Ile Ser Gly Glu Thr
    50                  55                  60

Asp Ser Leu Ile Ala Glu Gln Gly Ser Leu Arg Gly Asp Glu Asp Glu
65                  70                  75                  80

Ser Asp Asp Asp Asp Trp Glu Gly Val Glu Ser Thr Glu Leu Asp Glu
                85                  90                  95

Ala Phe Ser Ala Ala Thr Ala Phe Val Ala Ala Ala Ser Asp Arg
            100                 105                 110

Leu Ser Gln Lys Val Ser Asn Glu Leu Gln Leu Gln Leu Tyr Gly Leu
        115                 120                 125

Tyr Lys Ile Ala Thr Glu Gly Pro Cys Thr Ala Pro Gln Pro Ser Ala
    130                 135                 140

Leu Lys Met Thr Ala Arg Ala Lys Trp Gln Ala Trp Gln Lys Leu Gly
145                 150                 155                 160

Ala Met Pro Pro Glu Glu Ala Met Glu Lys Tyr Ile Asp Leu Val Thr
                165                 170                 175

Gln Leu Tyr Pro Ala Trp Val Glu Gly Ser Lys Arg Arg Asn Arg
            180                 185                 190

Ser Gly Glu Ala Ala Gly Pro Met Gly Pro Val Phe Ser Ser Leu Val
        195                 200                 205

Tyr Glu Glu Glu Ser Asp Asn Glu Leu Lys Ile Asp Ala Ile His Ala
    210                 215                 220
```

```
Phe Ala Arg Glu Gly Glu Val Glu Asn Leu Leu Lys Cys Ile Glu Asn
225                 230                 235                 240

Gly Ile Pro Val Asn Ala Arg Asp Ser Glu Gly Arg Thr Pro Leu His
            245                 250                 255

Trp Ala Ile Asp Arg Gly His Leu Asn Val Ala Glu Ala Leu Val Asp
            260                 265                 270

Lys Asn Ala Asp Val Asn Ala Lys Asp Asn Glu Gly Gln Thr Ser Leu
        275                 280                 285

His Tyr Ala Val Val Cys Glu Arg Glu Ala Leu Ala Glu Phe Leu Val
    290                 295                 300

Lys Gln Lys Ala Asp Thr Thr Ile Lys Asp Glu Asp Gly Asn Ser Pro
305                 310                 315                 320

Leu Asp Leu Cys Glu Ser Glu Trp Ser Trp Met Arg Glu Lys Lys Asp
                325                 330                 335

Ser Asn

<210> SEQ ID NO 28
<211> LENGTH: 354
<212> TYPE: PRT
<213> ORGANISM: Arabidopsis

<400> SEQUENCE: 28

Met Gly Asp Trp Ala Gln Leu Ala Gln Ser Val Ile Leu Gly Leu Ile
1               5                   10                  15

Phe Ser Tyr Leu Leu Ala Lys Leu Ile Ser Ile Val Val Thr Phe Lys
            20                  25                  30

Glu Asp Asn Leu Ser Leu Thr Arg His Pro Glu Glu Ser Gln Leu Glu
        35                  40                  45

Ile Lys Pro Glu Gly Val Asp Ser Arg Arg Leu Asp Ser Ser Cys Gly
    50                  55                  60

Gly Phe Gly Gly Glu Ala Asp Ser Leu Val Ala Glu Gln Gly Ser Ser
65                  70                  75                  80

Arg Ser Asp Ser Val Ala Gly Asp Asp Ser Glu Glu Asp Asp Asp Trp
                85                  90                  95

Glu Gly Val Glu Ser Thr Glu Leu Asp Glu Ala Phe Ser Ala Ala Thr
            100                 105                 110

Leu Phe Val Thr Thr Ala Ala Ala Asp Arg Leu Ser Gln Lys Val Pro
        115                 120                 125

Ser Asp Val Gln Gln Gln Leu Tyr Gly Leu Tyr Lys Ile Ala Thr Glu
    130                 135                 140

Gly Pro Cys Thr Ala Pro Gln Pro Ser Ala Leu Lys Met Thr Ala Arg
145                 150                 155                 160

Ala Lys Trp Gln Ala Trp Gln Lys Leu Gly Ala Met Pro Pro Glu Glu
                165                 170                 175

Ala Met Glu Lys Tyr Ile Glu Ile Val Thr Gln Leu Tyr Pro Thr Trp
            180                 185                 190

Leu Asp Gly Gly Val Lys Ala Gly Ser Arg Gly Gly Asp Asp Ala Ala
        195                 200                 205

Ser Asn Ser Arg Gly Thr Met Gly Pro Val Phe Ser Ser Leu Val Tyr
    210                 215                 220

Asp Glu Glu Ser Glu Asn Glu Leu Lys Ile Asp Ala Ile His Gly Phe
225                 230                 235                 240

Ala Arg Glu Gly Glu Val Glu Asn Leu Leu Lys Ser Ile Glu Ser Gly
                245                 250                 255
```

```
Ile Pro Val Asn Ala Arg Asp Ser Glu Gly Arg Thr Pro Leu His Trp
        260                 265                 270

Ala Ile Asp Arg Gly His Leu Asn Ile Ala Lys Val Leu Val Asp Lys
    275                 280                 285

Asn Ala Asp Val Asn Ala Lys Asp Asn Glu Gly Gln Thr Pro Leu His
290                 295                 300

Tyr Ala Val Val Cys Asp Arg Glu Ala Ile Ala Glu Phe Leu Val Lys
305                 310                 315                 320

Gln Asn Ala Asn Thr Ala Ala Lys Asp Glu Asp Gly Asn Ser Pro Leu
                325                 330                 335

Asp Leu Cys Glu Ser Asp Trp Pro Trp Ile Arg Asp Ser Ala Lys Gln
            340                 345                 350

Ala Asp

<210> SEQ ID NO 29
<211> LENGTH: 362
<212> TYPE: PRT
<213> ORGANISM: Arabidopsis

<400> SEQUENCE: 29

Met Glu Val Phe Leu Glu Met Leu Leu Thr Ala Val Val Ala Leu Leu
1               5                   10                  15

Phe Ser Phe Leu Leu Ala Lys Leu Val Ser Val Ala Thr Val Glu Asn
            20                  25                  30

Asp Leu Ser Ser Asp Gln Pro Leu Lys Pro Glu Ile Gly Val Gly Val
        35                  40                  45

Thr Glu Asp Val Arg Phe Gly Met Lys Met Asp Ala Arg Val Leu Glu
    50                  55                  60

Ser Gln Arg Asn Phe Gln Val Val Asp Glu Asn Val Glu Leu Val Asp
65                  70                  75                  80

Arg Phe Leu Ser Glu Glu Ala Asp Arg Val Tyr Glu Val Asp Glu Ala
                85                  90                  95

Val Thr Gly Asn Ala Lys Ile Cys Gly Asp Arg Glu Ala Glu Ser Ser
            100                 105                 110

Ala Ala Ala Ser Ser Glu Asn Tyr Val Ile Ala Glu Val Ile Leu
        115                 120                 125

Val Arg Gly Gln Asp Glu Gln Ser Asp Ser Ala Glu Ala Glu Ser Ile
    130                 135                 140

Ser Ser Val Ser Pro Glu Asn Val Val Ala Glu Ile Lys Ser Gln
145                 150                 155                 160

Gly Gln Glu Glu Val Thr Glu Leu Gly Arg Ser Gly Cys Val Glu Asn
                165                 170                 175

Glu Glu Ser Gly Gly Asp Val Leu Val Ala Glu Ser Glu Glu Val Arg
            180                 185                 190

Val Glu Lys Ser Ser Asn Met Val Glu Glu Ser Asp Ala Glu Ala Glu
        195                 200                 205

Asn Glu Glu Lys Thr Glu Leu Thr Ile Glu Glu Asp Asp Asp Trp Glu
    210                 215                 220

Gly Ile Glu Arg Ser Glu Leu Glu Lys Ala Phe Ala Ala Ala Val Asn
225                 230                 235                 240

Leu Leu Glu Glu Ser Gly Lys Ala Glu Glu Ile Gly Ala Glu Ala Lys
                245                 250                 255

Met Glu Leu Phe Gly Leu His Lys Ile Ala Thr Glu Gly Ser Cys Arg
            260                 265                 270
```

```
Glu Ala Gln Pro Met Ala Val Met Ile Ser Ala Arg Ala Lys Trp Asn
            275                 280                 285

Ala Trp Gln Lys Leu Gly Asn Met Ser Gln Glu Glu Ala Met Glu Gln
        290                 295                 300

Tyr Leu Ala Leu Val Ser Lys Glu Ile Pro Gly Leu Thr Lys Ala Gly
305                 310                 315                 320

His Thr Val Gly Lys Met Ser Glu Met Glu Thr Ser Val Gly Leu Pro
                325                 330                 335

Pro Asn Ser Gly Ser Leu Glu Asp Pro Thr Asn Leu Val Thr Thr Gly
            340                 345                 350

Val Asp Glu Ser Ser Lys Asn Gly Ile Pro
            355                 360

<210> SEQ ID NO 30
<211> LENGTH: 668
<212> TYPE: PRT
<213> ORGANISM: Arabidopsis

<400> SEQUENCE: 30

Met Ala Met Pro Arg Ala Thr Ser Gly Pro Ala Tyr Pro Glu Arg Phe
1               5                   10                  15

Tyr Ala Ala Ala Ser Tyr Val Gly Leu Asp Gly Ser Asp Ser Ser Ala
                20                  25                  30

Lys Asn Val Ile Ser Lys Phe Pro Asp Asp Thr Ala Leu Leu Leu Tyr
            35                  40                  45

Ala Leu Tyr Gln Gln Ala Thr Val Gly Pro Cys Asn Thr Pro Lys Pro
        50                  55                  60

Ser Ala Trp Arg Pro Val Glu Gln Ser Lys Trp Lys Ser Trp Gln Gly
65                  70                  75                  80

Leu Gly Thr Met Pro Ser Ile Glu Ala Met Arg Leu Phe Val Lys Ile
                85                  90                  95

Leu Glu Glu Asp Asp Pro Gly Trp Tyr Ser Arg Ala Ser Asn Asp Ile
            100                 105                 110

Pro Asp Pro Val Val Asp Val Gln Ile Asn Arg Ala Lys Asp Glu Pro
        115                 120                 125

Val Val Glu Asn Gly Ser Thr Phe Ser Glu Thr Lys Thr Ile Ser Thr
    130                 135                 140

Glu Asn Gly Arg Leu Ala Glu Thr Gln Asp Lys Asp Val Val Ser Glu
145                 150                 155                 160

Asp Ser Asn Thr Val Ser Val Tyr Asn Gln Trp Thr Ala Pro Gln Thr
                165                 170                 175

Ser Gly Gln Arg Pro Lys Ala Arg Tyr Glu His Gly Ala Ala Val Ile
            180                 185                 190

Gln Asp Lys Met Tyr Ile Tyr Gly Gly Asn His Asn Gly Arg Tyr Leu
        195                 200                 205

Gly Asp Leu His Val Leu Asp Leu Lys Ser Trp Thr Trp Ser Arg Val
    210                 215                 220

Glu Thr Lys Val Ala Thr Gly Ser Gln Glu Thr Ser Thr Pro Thr Leu
225                 230                 235                 240

Leu Ala Pro Cys Ala Gly His Ser Leu Ile Ala Trp Asp Asn Lys Leu
                245                 250                 255

Leu Ser Ile Gly Gly His Thr Lys Asp Pro Ser Glu Ser Met Gln Val
            260                 265                 270

Lys Val Phe Asp Pro His Thr Ile Thr Trp Ser Met Leu Lys Thr Tyr
```

```
                275                 280                 285
Gly Lys Pro Pro Val Ser Arg Gly Gly Gln Ser Val Thr Met Val Gly
    290                 295                 300

Lys Thr Leu Val Ile Phe Gly Gly Gln Asp Ala Lys Arg Ser Leu Leu
305                 310                 315                 320

Asn Asp Leu His Ile Leu Asp Leu Asp Thr Met Thr Trp Asp Glu Ile
                325                 330                 335

Asp Ala Val Gly Val Ser Pro Ser Pro Arg Ser Asp His Ala Ala Ala
            340                 345                 350

Val His Ala Glu Arg Phe Leu Leu Ile Phe Gly Gly Ser His Ala
        355                 360                 365

Thr Cys Phe Asp Asp Leu His Val Leu Asp Leu Gln Thr Met Glu Trp
370                 375                 380

Ser Arg Pro Ala Gln Gln Gly Asp Ala Pro Thr Pro Arg Ala Gly His
385                 390                 395                 400

Ala Gly Val Thr Ile Gly Glu Asn Trp Phe Ile Val Gly Gly Gly Asp
                405                 410                 415

Asn Lys Ser Gly Ala Ser Glu Ser Val Val Leu Asn Met Ser Thr Leu
            420                 425                 430

Ala Trp Ser Val Val Ala Ser Val Gln Gly Arg Val Pro Leu Ala Ser
        435                 440                 445

Glu Gly Leu Ser Leu Val Val Ser Ser Tyr Asn Gly Glu Asp Val Leu
    450                 455                 460

Val Ala Phe Gly Gly Tyr Asn Gly Arg Tyr Asn Asn Glu Ile Asn Leu
465                 470                 475                 480

Leu Lys Pro Ser His Lys Ser Thr Leu Gln Thr Lys Thr Leu Glu Ala
                485                 490                 495

Pro Leu Pro Gly Ser Leu Ser Ala Val Asn Asn Ala Thr Thr Arg Asp
            500                 505                 510

Ile Glu Ser Glu Val Glu Val Ser Gln Glu Gly Arg Val Arg Glu Ile
        515                 520                 525

Val Met Asp Asn Val Asn Pro Gly Ser Lys Val Glu Gly Asn Ser Glu
    530                 535                 540

Arg Ile Ile Ala Thr Ile Lys Ser Glu Lys Glu Glu Leu Glu Ala Ser
545                 550                 555                 560

Leu Asn Lys Glu Arg Met Gln Thr Leu Gln Leu Arg Gln Glu Leu Gly
                565                 570                 575

Glu Ala Glu Leu Arg Asn Thr Asp Leu Tyr Lys Glu Leu Gln Ser Val
            580                 585                 590

Arg Gly Gln Leu Ala Ala Glu Gln Ser Arg Cys Phe Lys Leu Glu Val
        595                 600                 605

Asp Val Ala Glu Leu Arg Gln Lys Leu Gln Thr Leu Glu Thr Leu Gln
    610                 615                 620

Lys Glu Leu Glu Leu Leu Gln Arg Gln Lys Ala Ala Ser Glu Gln Ala
625                 630                 635                 640

Ala Met Asn Ala Lys Arg Gln Gly Ser Gly Val Trp Gly Trp Leu
                645                 650                 655

Ala Gly Ser Pro Gln Glu Lys Asp Asp Asp Ser Pro
            660                 665

<210> SEQ ID NO 31
<211> LENGTH: 648
<212> TYPE: PRT
<213> ORGANISM: Arabidopsis
```

<400> SEQUENCE: 31

```
Met Ala His Met Val Arg Ala Ser Ser Gly Leu Ser Tyr Pro Glu Arg
1               5                   10                  15

Phe Tyr Ala Ala Ala Ser Tyr Val Gly Leu Asp Gly Ser Gln Ser Ser
            20                  25                  30

Val Lys Gln Leu Ser Ser Lys Phe Ser Asn Asp Thr Ser Leu Leu Leu
        35                  40                  45

Tyr Thr Leu His Gln Gln Ala Thr Leu Gly Pro Cys Ser Ile Pro Lys
    50                  55                  60

Pro Ser Ala Trp Asn Pro Val Glu Gln Ser Lys Trp Lys Ser Trp Gln
65                  70                  75                  80

Gly Leu Gly Thr Met Pro Ser Ile Glu Ala Met Arg Leu Phe Val Lys
                85                  90                  95

Ile Leu Glu Glu Ala Asp Pro Gly Trp Tyr Pro Arg Thr Ser Asn Ser
            100                 105                 110

Val Leu Asp Pro Ala Val His Val Gln Ile Asn Ser Thr Lys Ala Glu
        115                 120                 125

Pro Ser Phe Glu Ser Gly Ala Ser Phe Gly Thr Lys Thr Ile Thr
    130                 135                 140

Ser Glu Asp Gly Arg Leu Thr Glu Thr Gln Asp Lys Asp Val Val Leu
145                 150                 155                 160

Glu Asp Pro Asp Thr Val Ser Val Tyr Asn Gln Trp Thr Ala Pro Arg
                165                 170                 175

Thr Ser Gly Gln Pro Pro Lys Ala Arg Tyr Gln His Gly Ala Ala Val
            180                 185                 190

Ile Gln Asp Lys Met Tyr Met Tyr Gly Gly Asn His Asn Gly Arg Tyr
        195                 200                 205

Leu Gly Asp Leu His Val Leu Asp Leu Lys Asn Trp Thr Trp Ser Arg
    210                 215                 220

Val Glu Thr Lys Val Val Thr Gly Ser Gln Glu Thr Ser Ser Pro Ala
225                 230                 235                 240

Lys Leu Thr His Cys Ala Gly His Ser Leu Ile Pro Trp Asp Asn Gln
                245                 250                 255

Leu Leu Ser Ile Gly Gly His Thr Lys Asp Pro Ser Glu Ser Met Pro
            260                 265                 270

Val Met Val Phe Asp Leu His Cys Cys Ser Trp Ser Ile Leu Lys Thr
        275                 280                 285

Tyr Gly Lys Pro Pro Ile Ser Arg Gly Gly Gln Ser Val Thr Leu Val
    290                 295                 300

Gly Lys Ser Leu Val Ile Phe Gly Gly Gln Asp Ala Lys Arg Ser Leu
305                 310                 315                 320

Leu Asn Asp Leu His Ile Leu Asp Leu Asp Thr Met Thr Trp Glu Glu
                325                 330                 335

Ile Asp Ala Val Gly Ser Pro Pro Thr Pro Arg Ser Asp His Ala Ala
            340                 345                 350

Ala Val His Ala Glu Arg Tyr Leu Leu Ile Phe Gly Gly Gly Ser His
        355                 360                 365

Ala Thr Cys Phe Asp Asp Leu His Val Leu Asp Leu Gln Thr Met Glu
    370                 375                 380

Trp Ser Arg His Thr Gln Gln Gly Asp Ala Pro Thr Pro Arg Ala Gly
385                 390                 395                 400

His Ala Gly Val Thr Ile Gly Glu Asn Trp Tyr Ile Val Gly Gly Gly
```

-continued

```
            405                 410                 415
Asp Asn Lys Ser Gly Ala Ser Lys Thr Val Val Leu Asn Met Ser Thr
            420                 425                 430

Leu Ala Trp Ser Val Val Thr Ser Val Gln Glu His Val Pro Leu Ala
            435                 440                 445

Ser Glu Gly Leu Ser Leu Val Val Ser Ser Tyr Asn Gly Glu Asp Ile
            450                 455                 460

Val Val Ala Phe Gly Gly Tyr Asn Gly His Tyr Asn Asn Glu Val Asn
465                 470                 475                 480

Val Leu Lys Pro Ser His Lys Ser Ser Leu Lys Ser Lys Ile Met Gly
            485                 490                 495

Ala Ser Ala Val Pro Asp Ser Phe Ser Ala Val Asn Asn Ala Thr Thr
            500                 505                 510

Arg Asp Ile Glu Ser Glu Ile Lys Val Glu Gly Lys Ala Asp Arg Ile
            515                 520                 525

Ile Thr Thr Leu Lys Ser Glu Lys Glu Val Glu Ala Ser Leu Asn
            530                 535                 540

Lys Glu Lys Ile Gln Thr Leu Gln Leu Lys Glu Glu Leu Ala Glu Ile
545                 550                 555                 560

Asp Thr Arg Asn Thr Glu Leu Tyr Lys Glu Leu Gln Ser Val Arg Asn
            565                 570                 575

Gln Leu Ala Ala Glu Gln Ser Arg Cys Phe Lys Leu Glu Val Glu Val
            580                 585                 590

Ala Glu Leu Arg Gln Lys Leu Gln Thr Met Glu Thr Leu Gln Lys Glu
            595                 600                 605

Leu Glu Leu Leu Gln Arg Gln Arg Ala Val Ala Ser Glu Gln Ala Ala
            610                 615                 620

Thr Met Asn Ala Lys Arg Gln Ser Ser Gly Gly Val Trp Gly Trp Leu
625                 630                 635                 640

Ala Gly Thr Pro Pro Pro Lys Thr
            645
```